United States Patent
McCarthy et al.

(10) Patent No.: US 10,556,074 B2
(45) Date of Patent: Feb. 11, 2020

(54) ARTIFICIAL RESPIRATION SYSTEM WITH TIMING CONTROL AND AUTOMATIC MASK DETECTION

(71) Applicants: Daniel A. McCarthy, Tyler, TX (US); Michael D. Rainone, Palestine, TX (US); Samuel Albert Sackett, Frankston, TX (US); Adam Collin Vance, Palenstine, TX (US); Phillip Ryan Grisham, Bullard, TX (US)

(72) Inventors: Daniel A. McCarthy, Tyler, TX (US); Michael D. Rainone, Palestine, TX (US); Samuel Albert Sackett, Frankston, TX (US); Adam Collin Vance, Palenstine, TX (US); Phillip Ryan Grisham, Bullard, TX (US)

(73) Assignee: Daniel A. McCarthy, Tyler, TX (US)

( * ) Notice: Subject to any disclaimer, the term of this patent is extended or adjusted under 35 U.S.C. 154(b) by 781 days.

(21) Appl. No.: 15/213,087

(22) Filed: Jul. 18, 2016

(65) Prior Publication Data
US 2017/0143932 A1    May 25, 2017

Related U.S. Application Data

(60) Provisional application No. 62/302,490, filed on Mar. 2, 2016, provisional application No. 62/193,811, filed on Jul. 17, 2015.

(51) Int. Cl.
*A61M 16/00* (2006.01)
*A61M 16/06* (2006.01)
*A61M 16/08* (2006.01)

(52) U.S. Cl.
CPC .... *A61M 16/0051* (2013.01); *A61M 16/0605* (2014.02); *A61M 16/0816* (2013.01);
(Continued)

(58) Field of Classification Search
CPC .................. A61M 16/0084; A61M 16/0078
See application file for complete search history.

(56) References Cited

U.S. PATENT DOCUMENTS

| 3,613,677 A | 10/1971 | Blasko |
| 4,196,725 A | 4/1980 | Gunderson |

(Continued)

FOREIGN PATENT DOCUMENTS

| JP | 11178924 | 6/1999 |
| WO | 2010042677 | 4/2010 |

OTHER PUBLICATIONS

Impact Model 706 Specifications, Sep. 2003. (1 page).
(Continued)

*Primary Examiner* — Tan-Uyen T Ho
*Assistant Examiner* — Cana A Gallegos
(74) *Attorney, Agent, or Firm* — Kowert, Hood, Munyon, Rankin & Goetzel, P.C.; Mark R. DeLuca

(57) ABSTRACT

A ventilator system and method can deliver artificial respirations to a person receiving cardiopulmonary resuscitation. The system and method may provide intermittent breath delivery (e.g., with interruptions), so that activation of the device gives a specific predetermined number of breaths, interspersed with a set time period of no breath. This pattern may be by default, manually triggered where one activation gives a set number of breaths followed by a pause until the next activation for breath (one activation gives one breath cycle), or one activation results in continuous cycle of intermittent breaths). In some embodiments, a signaling mechanism may deliver signals to a rescuer relating to timing of chest compressions of the person. The timing of the chest compressions for the signals may be based on a time of delivery of the artificial respirations. In certain embodiments, different sized masks each include a gas flow restrictor which is unique for the size of mask. The ventilator (Continued)

system may assess the size of the mask based on a pressure differential created by the unique gas flow restrictor.

17 Claims, 18 Drawing Sheets

(52) U.S. Cl.
CPC . *A61M 2016/0027* (2013.01); *A61M 2205/14* (2013.01); *A61M 2240/00* (2013.01)

(56) References Cited

U.S. PATENT DOCUMENTS

| | | | |
|---|---|---|---|
| 4,226,234 A | 10/1980 | Gunderson | |
| 4,297,999 A | 11/1981 | Kitrell | |
| 4,693,242 A | 9/1987 | Biard | |
| 4,863,385 A | 9/1989 | Pierce | |
| 5,211,170 A | 5/1993 | Press | |
| 5,398,676 A | 3/1995 | Press et al. | |
| 5,460,174 A | 10/1995 | Chang | |
| 5,651,361 A | 7/1997 | Dearman et al. | |
| 5,738,088 A | 4/1998 | Townsend | |
| 5,810,001 A | 9/1998 | Gengal et al. | |
| 5,944,013 A | 8/1999 | Burch | |
| 5,979,444 A | 11/1999 | Sherrod | |
| 6,213,120 B1 | 4/2001 | Block et al. | |
| 6,378,517 B1 | 4/2002 | Steen | |
| 6,405,728 B1 | 6/2002 | Van Hall et al. | |
| 6,742,399 B2 | 6/2004 | Kunz et al. | |
| 6,895,959 B2 | 5/2005 | Lukas | |
| 6,895,962 B2 | 5/2005 | Kullik et al. | |
| 6,929,006 B2 | 8/2005 | Kruger et al. | |
| 7,093,596 B2 | 8/2006 | Muller et al. | |
| 7,331,339 B2 | 2/2008 | Smith et al. | |
| 7,367,338 B2 | 5/2008 | Baecke et al. | |
| 7,497,731 B2 | 3/2009 | Rosenfeldt et al. | |
| 7,575,004 B2 | 8/2009 | Weich et al. | |
| 7,578,293 B2 | 8/2009 | Matthiessen et al. | |
| 7,770,581 B2 | 8/2010 | Balke et al. | |
| 2003/0165794 A1 | 9/2003 | Matoba | |
| 2004/0118403 A1 | 6/2004 | O'Connor et al. | |
| 2005/0085799 A1 | 4/2005 | Luria et al. | |
| 2005/0092324 A1 | 5/2005 | Bowden et al. | |
| 2005/0284469 A1 | 12/2005 | Tobia et al. | |
| 2006/0278222 A1 | 12/2006 | Schermeier et al. | |
| 2007/0044805 A1 | 3/2007 | Wedler et al. | |
| 2008/0000478 A1 | 1/2008 | Matthiessen et al. | |
| 2008/0053445 A1 | 3/2008 | Kroupa et al. | |
| 2008/0078387 A1 | 4/2008 | Vandine | |
| 2008/0200776 A1 | 8/2008 | Schermeier et al. | |
| 2008/0264417 A1 | 10/2008 | Manigel et al. | |
| 2009/0320850 A1 | 12/2009 | Wallnewitz et al. | |
| 2010/0094366 A1 | 4/2010 | McCarthy | |
| 2010/0147306 A1 | 6/2010 | Townsend et al. | |
| 2012/0247470 A1* | 10/2012 | Ho | A61M 16/0051 128/204.21 |
| 2018/0333548 A1 | 11/2018 | Nadkarni et al. | |

OTHER PUBLICATIONS

Impact Uni-Vent 706 from Emergency Medical Products (http://www.buyemp.com/product/1020803.html), Jun. 6, 2008. (1 page).
"O-Two Medical Technologies Inc." accessed at <http://www.otwo.com/prod_par.htm>, Jan. 22, 2010. (2 pages).
"CAREvent PAR." Mar. 2008. (2 pages).
International Search Report and Written Opinion for PCT/US2009/059926 dated Jun. 22, 2010. (pp. 1-10).
International Preliminary Report on Patentability for PCT/US2009/059926 dated Apr. 21, 2011. (pp. 1-5).
Office Action for U.S. Appl. No. 15/447,698 dated Mar. 7, 2019.

* cited by examiner

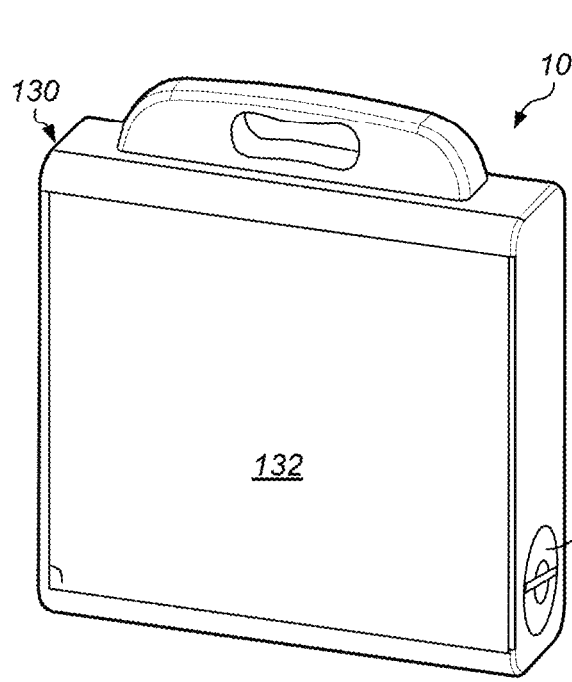
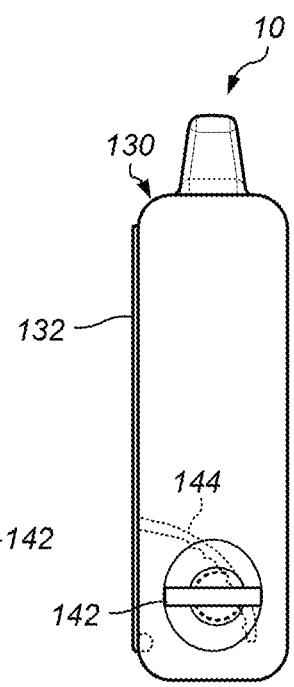
FIG. 6A　　FIG. 6B
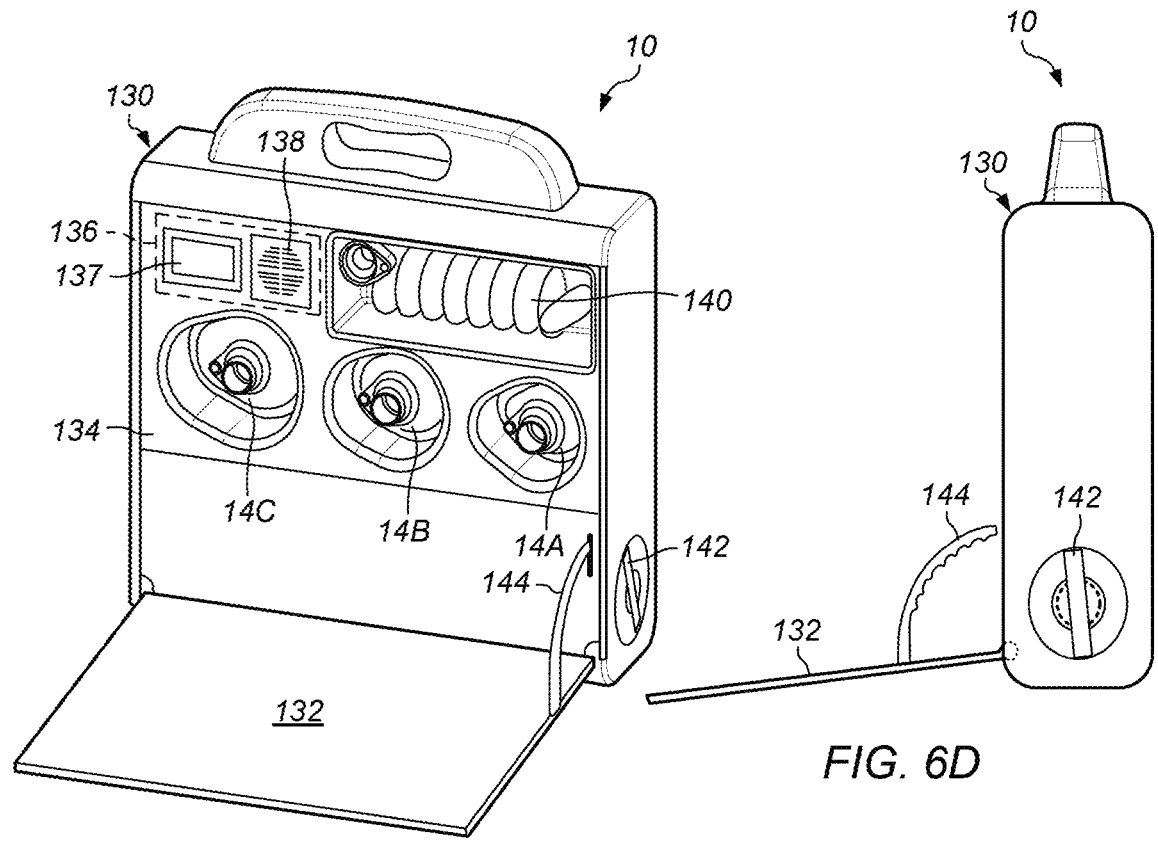
FIG. 6C　　FIG. 6D

ARTIFICIAL RESPIRATION SYSTEM WITH TIMING CONTROL AND AUTOMATIC MASK DETECTION

PRIORITY CLAIM

This application claims priority to U.S. Provisional Patent Application No. 62/302,490 entitled "ARTIFICIAL RESPIRATION SYSTEM AND METHOD HAVING AUTOMATIC MASK DETECTION" filed on Mar. 2, 2016, and U.S. Provisional Patent Application No. 62/193,811 entitled "PERFORMING CPR WITH CONTROL OF TIMING OF RESPIRATIONS AND COMPRESSIONS" filed on Jul. 17, 2015, both of which are incorporated by reference as if fully set forth herein.

BACKGROUND

1. Field of the Invention

The present invention generally relates to a system and method for providing air/oxygen to a subject, and more particularly to providing air/oxygen flow from an air/oxygen supply based on the size of a mask coupled to the air/oxygen supply. Certain embodiments of the invention relate to methods and systems for performing cardiopulmonary resuscitation (CPR), and more particularly methods and systems of timing chest compressions and artificial respirations during CPR.

2. Description of Related Art

Medical emergencies often call on one or more persons to provide life-saving support. For example, CPR may be performed when a person is not breathing, or breathing inadequately (e.g., during cardiac arrest). CPR generally involves providing air into a person's lungs via the mouth, or mouth and nose, and performing a series of chest compressions. This may be performed repeatedly to help oxygenate and circulate the blood. Blowing air into the victim's mouth forces air into the lungs to replace spontaneous respiration and compressing the chest compresses the heart to maintain blood circulation. In a situation in which the heart has stopped beating, performing CPR is intended to maintain a flow of oxygenated blood to the brain and heart, thereby delaying tissue death and extending the opportunity for a successful resuscitation without permanent brain damage. Defibrillation and other advanced life support techniques may also be used to improve the outcome for a victim of cardiac arrest.

CPR techniques can vary depending on the person needing assistance. For example, administering CPR to an adult generally includes providing a set number of full breaths via the mouth, whereas administering CPR to an infant or child may require a larger number of smaller breaths or puffs via the mouth and/or nose. The lower pressure and larger numbers of breaths administered to an infant or child may reduce the likelihood of injury to the respiratory system of the infant or child. Similarly, the force used in administering the chest compressions is reduced when administering CPR to an infant or child. Accordingly, a person who administers CPR must consider several variables and remember a variety of protocols.

CPR is more effective the sooner it is initiated and thus, the time between the onset of the medical emergency and the time of initiating CPR may be critical. Brain cells may begin to die in as little as 4-6 minutes without an adequate supply of oxygen. Unfortunately, medical emergencies can, and often do, happen at locations that are remote to medical facilities and where no trained medical professionals are readily available and, thus, a by-stander may be in the best position to perform CPR.

Although many people have some form of CPR training, it is believed that a large percentage of the population does not have adequate familiarity with or adequate training in CPR, or they lack sufficient ongoing practice required to maintain skill performance, and may not be capable of performing CPR properly. Skill retention is a serious issue in the ability to successfully perform CPR. As a result, when a medical emergency arises, CPR may be performed incorrectly and can lead to injury of the person in need of help. For example, a by-stander who untrained or inadequately trained, and who attempts to provide CPR to an infant may inadvertently provide full breaths, as opposed to light puffs. As mentioned above, the full breaths may cause damage to the infant's respiratory system. Further, in the stress of an emergency, the chance that a person becomes overwhelmed by this situation and becomes unable to perform CPR correctly and effectively is greatly increased. Also, it is believed that even with training, some people may be unwilling to perform CPR, especially to someone who is not a friend or family member. For example, a by-stander may have fears of becoming infected through bodily contact with a stranger and, as a result, the by-stander may not attempt CPR on the affected person. The lack of a willingness to perform CPR, and/or the inability to perform CPR correctly can seriously jeopardize the health and safety of those in need of assistance. Further, even when performed correctly, the amount of oxygen that can be delivered by mouth-to-mouth breathing may be significantly less than the amount of oxygen needed in an emergency.

During the compression phase of CPR, blood is moved from the heart into the aorta. The push of blood into the aorta causes the aorta to stretch. The pressure developed by this stretched aorta provides the necessary force to maintain the forward flow of blood during the respiration phase. The pressure quickly dissipates however. Consequently, there is considerable value in minimizing the non-compression (respiratory) phase of CPR.

Current CPR recommendations call for 30 compressions and two breaths in a cyclic pattern. The compression rate is currently specified at 100 compressions per minute. This rate gives an average compression time of roughly 0.6 seconds/compression. Thus, 30 compressions can be done in about 18 seconds. For adult artificial respirations, two breaths should be given over 6 seconds each, 1 second for positive pressure breath delivery followed by 5 seconds of passive exhalation—a total of 12 seconds for the respiratory phase. Current recommendations are that compressions should not be performed during the positive pressure phase of the respiratory cycle, as it is thought that this can lead to vomiting and aspiration.

In a ventilator that cycles continuously, during the compression phase of a typical resuscitation, the rescuer using the device to perform artificial respiration releases the seal on the mask from the face just enough to allow the breath to be vented to the environment and not to the lungs. Assuming, for this example, 18 seconds to perform 30 compressions, if one begins compressions as soon as the positive pressure phase of the breath is delivered and mask seal is released, the compressions finish 18 seconds later, again when the positive pressure phase is finished. This will result in a 5 second delay before the next breath, and a time when no compressions are given. This will result in a total of 12 seconds when no compressions are given (5 second expiratory phase, 6 second breath, 1 second inspiratory phase), an undesirably long total period. Thus, if 18 seconds are used for compressions, and 12 seconds for artificial respirations, this means that 40% of the time is spent in the respiratory phase.

While actually performing CPR, it would be difficult to determine the point of the ventilator cycle by watching the patient, especially when the breath is vented to the environment during the compression phase. As such, in a typical ventilator system that runs continuously, the person doing the chest compressions will not be sure what point of the respiratory cycle you will be at when the compressor finishes the prescribed number of compressions. To minimize the non compression, non ventilation time, beginning the compression phase at the immediate end of the positive pressure phase of the respiratory cycle may be important.

SUMMARY

Some embodiments of the present technique include a system and method for automatically providing air and/or oxygen in accordance with a set of preset artificial respiration or ventilation parameters based on the size of the mask used to deliver the air/oxygen. In one embodiment, the method includes providing air/oxygen at a pre-selected pressure (e.g., a maximum pressure limit), breath volume and respiratory-rate as a function of the size of the mask coupled to an air/oxygen supply system. In some embodiments, an air/oxygen system includes a ventilator system having a ventilator mask and a ventilator supply. In one embodiment, the mask that is ultimately coupled to the ventilator supply is chosen from a plurality of mask sizes.

Some embodiments relate to systems and related apparatus for use in performing CPR, and methods for performing CPR and providing information to rescuers during CPR. In an embodiment, a ventilator system includes a ventilator and a signaling mechanism. The ventilator can deliver artificial respirations to a person receiving cardiopulmonary resuscitation in which one artificial respiration cycle includes an inspiration phase and an exhalation phase. The ventilator produces a positive pressure during the inspiration phase. The signaling mechanism delivers signals to a rescuer relating to timing of chest compressions of the person. The timing of the chest compressions for the signals is based on a time of delivery of the artificial respirations. The signals to the person performing compressions may be timed to reduce the amount of non-compression, non-respiration time during CPR. In various embodiments, a system includes one or more masks that can be coupled to the device that supplies air/oxygen and/or controls the artificial respirations, signaling, or both. The air/oxygen sources (e.g., oxygen tanks) may be built into the device or provided separately.

In an embodiment, a method of providing information to rescuers for performing cardiopulmonary resuscitation includes assessing timing of artificial respirations delivered by a ventilator to a person during cardio pulmonary resuscitation, and providing to a rescuer a signal for the timing of chest compressions for the person. The timing of the chest compressions for the signals is based on a time of delivery of the artificial respirations.

In an embodiment, a method of performing cardiopulmonary resuscitation includes delivering, by a ventilator, artificial respirations to a person receiving cardiopulmonary resuscitation. A rescuer is provided with signals relating to timing of chest compressions for the person. The timing of the chest compressions signal is based on a time of delivery of at least one of the artificial respirations.

In an embodiment, a ventilator system includes a ventilator that can perform artificial respirations on a person during cardiopulmonary resuscitation, in which one artificial respiration cycle comprises an inspiration phase and an exhalation phase. The ventilator produces a positive pressure during the inspiration phase. In response to an activation (for example, pressing a manual trigger, or the initiation of oxygen flow), the ventilator delivers a pre-determined number of inspiration phases to the person, followed by at least one interval without delivering inspirations. This would result in a continuous sequence of ventilatory cycles with fixed intermittent pause in the ventilation to allow for chest compression.

In an embodiment, a method of performing cardiopulmonary resuscitation includes providing a ventilator that performs artificial respirations on a person. Each artificial respiration cycle includes an inspiration phase and an exhalation phase. A first series of chest compressions maybe performed on the person. In response to an activation of the ventilator (for example, pressing of a manual trigger), a predetermined number of inspiration phases of artificial respiration are delivered. At the end of the last inspiration phase of the predetermined number of inspiration phases, a second series of chest compressions on the person. This would result in one series of breaths for each activation of the ventilator.

BRIEF DESCRIPTION OF THE DRAWINGS

FIGS. 6A-6E are illustrations of a portable ventilator system in accordance with embodiments.

DETAILED DESCRIPTION OF ILLUSTRATIVE EMBODIMENTS

Figure 1:
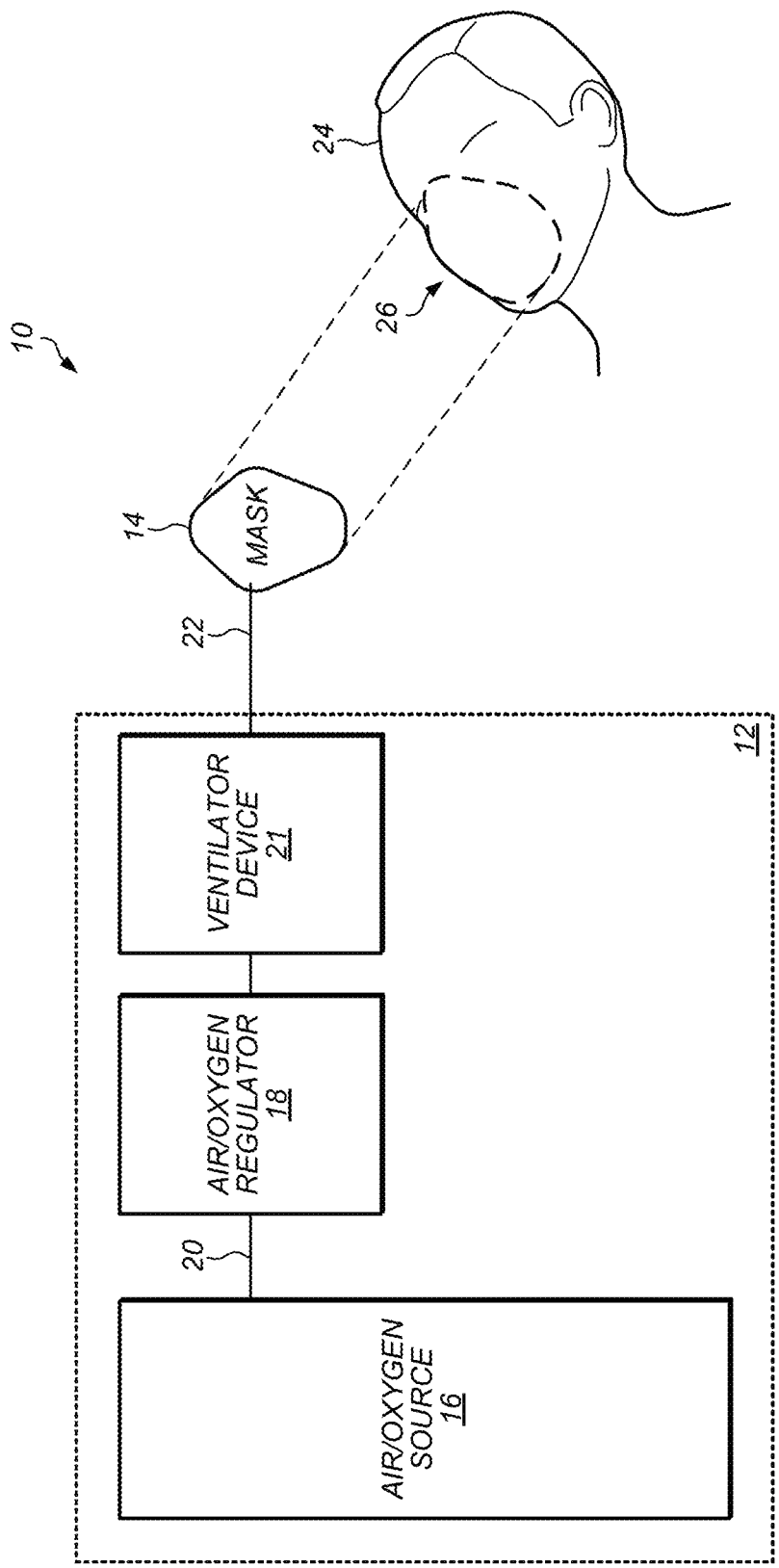
FIG. 1, depicted is a block diagram that illustrates a ventilator system.

As discussed in more detail below, certain embodiments of the present technique include a system and method for automatically providing air and/or oxygen in accordance with a set of preset artificial respiration or ventilation parameters based on the size of the mask used to deliver the air/oxygen. In one embodiment, the method includes providing air/oxygen at a pre-selected pressure (e.g., a maximum pressure limit), breath volume and respiratory-rate as a function of the size of the mask coupled to an air/oxygen supply system. In some embodiments, an air/oxygen system includes a ventilator system having a ventilator mask and a ventilator supply. In one embodiment, the mask that is ultimately coupled to the ventilator supply is chosen from a plurality of mask sizes. The mask sizes include, in some embodiments, an infant sized mask, a child sized mask and an adult sized mask. In certain embodiments, the ventilator system is configured to deliver the air/oxygen in accordance with ventilation parameters associated with the size of the mask that is currently coupled to the supply system of the ventilator. In certain embodiments, each different sized mask includes a gas flow restrictor which is unique for the size of mask. The ventilator system is therefore configured to assess the size of the mask based on a pressure differential created by the unique gas flow restrictor. Such a ventilator may be employed for use in the administration of artificial respiration during CPR. Before discussing embodiments of the present technique in detail, it may be beneficial to discuss embodiments of systems that may be configured to employ such a method and system.

In various embodiments, and as further described below, systems and methods for performing CPR implement measures to control timing of, and transitions between, artificial respirations and chest compressions. In some embodiments, a signaling system provides signals or instructions to the rescuers when to compress and when not to compress based on the respirations. Different signals may be provided for when to start and when to stop compressions and/or respirations. In some embodiments, the system provides audible instructions, such as "Start Compressions Now", "Stop Compressions Now", "Start Compressions in 3 . . . 2 . . . 1" etc. The timing of compressions may be selected to limit the amount of time of non-compression, non-respiration based on tgulhe operational characteristics of the ventilator being used to perform CPR.

In some embodiments, a system provides intermittent breath delivery (which may be as a default built into the device), so that activation of the device gives a specific predetermined number of breaths, interspersed with a time period of no breath. This pattern may manually triggered where one activation gives a set number of breaths followed by a pause until the next activation for breath (one activation gives one breath cycle), or one activation resulting in continuous cycle of intermittent breaths. Interruptions during intermittent breath delivery may, in various embodiments, be regular or irregular.

In various embodiments, a system uses signals given to a person performing compressions, manual control of the timing of respirations, or both, to reduce the amount of non-compression, non-respiration time during CPR. For example, the system and method may produce a two breath sequence with only about a 7 second interruption in compressions per cycle, instead of up to, for example, 12 second interruption per cycle.

Ventilator Systems and Methods of Using Ventilators

As discussed in more detail below, embodiments include systems and method for automatically providing air and/or oxygen during CPR. Turning now to FIG. 1, depicted is a block diagram that illustrates a ventilator system 10 in accordance with one or more embodiments. The ventilator system 10 includes a ventilator supply system 12 and a ventilator mask 14.

In the illustrated embodiment, the ventilator supply system 12 includes an air/oxygen source ("source") 16, an air/oxygen regulator ("regulator") 18, a supply conduit 20, a ventilation control system 21, and a mask conduit 22. As used herein, "ventilator system" refers to a system configured to mechanically move breathable air and/or oxygen (air/oxygen) into a subject's lungs, to provide artificial respiration for the subject who is not breathing, or breathing insufficiently. As used herein, a "ventilation control system" is a device that can be used to produce artificial respiration, alone or in combination with other components. A ventilation control system may include one or more mechanical, fluid (e.g., pneumatic), electronic components, or various combinations thereof, that provide artificial respiration. A ventilation control system may be coupled to a source of air/oxygen, such as source 16/regulator 18. A ventilation control system may be operated manually, automatically, or a combination thereof. A ventilation control system may include, or be coupled to, electronic control systems (a "controller"). In certain embodiments, a ventilation control system is entirely mechanical (e.g., without any electronic components). In certain embodiments, a ventilation control system is entirely pneumatic.

In operation, exhalation may occur passively due to normal chest wall recoil. As used herein, "air/oxygen" refers to atmospheric air, medically pure oxygen, or oxygen-enriched air. As used herein, "medically pure oxygen" refers to a gas having an oxygen concentration above approximately 90% by volume. As used herein, "oxygen-enriched air" refers to a gas having an oxygen concentration above that of atmospheric air. As used herein, "subject" refers to a person in need of supplemental air/oxygen and/or cardio pulmonary resuscitation (CPR).

In operation, the ventilator system 10 may provide a flow of air/oxygen to a subject 24. For instance, the ventilator system 10 may be employed to provide air/oxygen to a subject 24 during CPR. In other words, instead of providing artificial respiration by mouth-to-mouth breathing, physically blowing air/oxygen into the subject's mouth or by some other non-controlled technique, such as a squeezable resuscitation bag, the ventilator system 10 can be employed as the source of the air/oxygen administered to the subject 24 during CPR. In one such embodiment, the mask 14 is placed over a face region 26 of the subject 24, and the ventilator system 10 is operated to deliver air/oxygen from the source 16 to the subject 24 via the supply conduit 20, the regulator 18, ventilation control system 21, the mask conduit 22, and the mask 14.

In certain embodiments, the source 16 is capable of providing pressurized air/oxygen for use by the ventilator system 10. As used herein "pressurized air/oxygen" refers to air/oxygen having a pressure that promotes the flow of the air/oxygen from the ventilator system 10 into the lungs of the subject 24. Pressurized air/oxygen may have a pressure that is above a minimum-pressure threshold, such as 20 centimeters of water ($cmH_2O$) above ambient air pressure.

This pressurized air/oxygen may also serve to drive a pneumatic device like ventilation control system 21.

In one embodiment, the source 16 includes a cylinder containing the pressurized air/oxygen. The pressure of the air/oxygen may be set significantly above the minimum-pressure threshold such that the air/oxygen in the cylinder is maintained above the minimum-pressure threshold as the air/oxygen is expelled from the cylinder and the pressure of the air/oxygen in the source 16 drops as function of the air/oxygen expelled from the cylinder. The source 16 may include a mechanical device, such as a compressor, configured to move and/or pressurize the air/oxygen. Such a mechanical device may be used to pressurize and/or fill a cylinder of the source 16. In one embodiment, the source 16 may include the mechanical device to move the air from the cylinder to the subject.

In another embodiment, the device may receive air/oxygen from the surrounding atmosphere, another source (e.g., an oxygen separation, chemically generated oxygen, or enrichment device) or an air/gas cylinder. The device may, for example, compress the air/oxygen to a pressure above the minimum-pressure threshold before expelling it through the ventilator system 10. The ventilator system 10 may be configured such that the air/oxygen is expelled under pressure from the source 16 and is routed to the subject 24 via the supply conduit 20, the regulator 18, the ventilation control system 21, the mask conduit 22, and the mask 14.

The supply conduit 20 includes a path that directs the air/oxygen from an outlet of the source 16 to an inlet of the regulator 18. In an embodiment in which the source 16 and the regulator 18 are disposed directly adjacent to one another, the supply conduit 20 may include a channel formed by the outlet of the source 16 and the inlet of the air/oxygen regulator 18. In an embodiment in which the source 16 and the regulator 18 are not disposed directly adjacent to one another and/or a distance exists between the two, the supply conduit 20 may include a tube, pipe, or the like, that extends between the outlet of the source 16 and the inlet of the regulator 18. In one embodiment, the supply conduit 20 includes a flexible tube, such as plastic tubing. In another embodiment, the supply conduit 20 includes a rigid structure mounted between the source 16 and the regulator 18. For instance, in one embodiment, the supply conduit 20 includes a brass coupler that is disposed between the source 16 and the regulator 18. Coupling between the supply conduit 20, the source 16, and/or the regulator 18 can be provided via various forms of mechanical coupling, such as a threaded connection, an interference fit, a detent feature, an adhesive, or a combination thereof.

The source 16 and the regulator 18 may be removably coupled to one another and/or the supply conduit 20, in one embodiment. Such a configuration may enable independent replacement, reconditioning, and/or recharging of the source 16 and/or the regulator 18. For instance, in an embodiment in which the source 16 includes a cylinder that is empty or low (e.g., having an air/oxygen pressure below a minimum threshold pressure), the cylinder can be disconnected from the regulator 18, recharged with pressurized air/oxygen and reconnected to the regulator 18. In embodiments wherein the source 16 includes an oxygen enrichment and/or separation device, the source 16 can be disconnected and serviced. Where the source 16 includes a system to chemically generate oxygen, the source can be exchanged for fresh components.

The regulator 18 may regulate the air/oxygen flow from the source 16. In one embodiment, the ventilator system 10 includes one or more ventilation control systems 21 that impede the flow of the air/oxygen from the regulator 18, the supply conduit 20 and the source 16. By impeding the flow of the air/oxygen, the ventilation control system 21 may be used to control one or more flow or respiratory parameters of the air/oxygen. As used herein "flow parameters" or "respiratory parameters" refers to characteristics of gas or fluid flow including, but not limited to, pressure, "tidal" or "breath" volume, and breath frequency or rate and flow rate. As used herein "pressure" may refer to the maximum airway pressure (e.g., maximum pressure limit). The "maximum pressure limit" refers to the maximum pressure to which the subject receiving artificial respiration is exposed. As used herein, the "tidal volume" or "breath volume" refers to the volume of air/oxygen inspired during each normal cycle. As used herein, "respiratory-rate" refers to the number of breaths over a period of time (e.g., breaths per minute). These two parameters, tidal volume times respiratory rate, yield a result called minute ventilation, usually in liters per minute. This value corresponds to how much breath volume is delivered each minute. Flow rate is a measure of how fast the breath is given. For example, the American Heart Association recommends that for adult CPR the victim receive 10 breaths per minute with a volume of six hundred cc each.

In some cases, the breaths are given over one second with 5 seconds for passive exhalation. Breath volume times rate gives a minute ventilation of 6 L/M. The 600 cc breath is given over 1 second. This gives a flow rate of 600 cc/second. Because of the way the breaths are given, minute ventilation and flow rate may be equal. If it is determined that breaths should be delivered over 2 seconds with 4 seconds for passive exhalation, the minute ventilation would be the same, but the flow rate would be halved. Further, in an embodiment in which a cyclic air/flow is desired, the flow parameters may include an inspiratory time and an expiratory time. As used herein "inspiratory time" refers to time over which the tidal or breath volume is delivered, and "expiratory time" is the time between the end of one inspiratory cycle and beginning of the next inspiratory cycle.

In certain embodiments, the flow parameters may be indicative of the operation of the ventilator system 10. For example, the pressure of the air/oxygen contained by and/or expelled from the source 16 may be indicative of a failed or deficient supply of air/oxygen. In one embodiment, a drop in the air/oxygen pressure below a minimum threshold pressure indicates that the source 16 (e.g., the cylinder) needs to be replaced, recharged, or otherwise serviced.

During a ventilation cycle, the pressure in the airway may increase as air/oxygen is forced into the airway/lungs during an inspiratory/inhalation phase. During artificial respirations, it may be desired that the pressure in the airway remain low. Excess pressure can lead to trauma to the lungs and airway, increase gastric distention, or may be indicative of a blocked airway. Typically adults can tolerate higher airway pressures that infants and children. A pressure relief valve may vent pressure above a maximum pressure limit. In such an embodiment, the pressure at which the relief valve opens may vary from infant to child to adult. Further, excess flow beyond what is needed for proper ventilation function during artificial respiration may be expelled from the system via leakage around the mask 14, or shunting through a pressure relief valve. In one embodiment, a relief valve may be integral to the ventilation control system 21 and/or the mask 24, or the mask conduit 22, and may open as a function of a maximum pressure limit. In one embodiment, the air/oxygen flow may be configured at a minimum level for the subject 24. Such a configuration may reduce the amount of air/oxygen that is leaked or expelled. In a system that includes a finite amount of air/oxygen in the source 16, the reduced amount of air leaked or expelled may increase the duration of functioning of the ventilator supply system 10.

In certain embodiments, the regulator 18 includes a gauge that provides an indication of the air/oxygen pressure of the gas or fluid housed in the source 16. There may also be a gauge to provide information on the flow parameters of the air/oxygen contained by or being expelled from the regulator 18 and/or being delivered through the mask 14. In one embodiment, the current air/oxygen pressure is indicated by the gauge disposed on and/or integral to the pressure regulator 18. Other indicators can be provided in certain embodiments. For example, in one embodiment, a gauge is provided in coordination with a signal and/or alarm. The signal and/or alarm may be capable of alerting a user or other monitor, such as a person or maintenance system, that the ventilator system 10 is in need of service or repair. The signal and/or alarm may include visible markings, one or more lights, a buzzer, a siren, or the like. For instance, in one embodiment, the gauge may be indicative of the current pressure in the source 16 and have markings indicative of a high pressure, a safe pressure, and/or a low pressure.

Similarly, the pressure of the air/oxygen being delivered to the subject 24 may be indicative of the status of the air/oxygen being administered (e.g., the status of one or more observed flow parameters). In other words, the pressure may indicate whether the path of the air/oxygen is blocked or leaking. For example, an increase in the air/oxygen pressure downstream of the ventilation control system 21 may indicate that the air passage of the subject 24 is blocked (e.g., something is lodged in the subject's throat). Similarly, a drop in the pressure below a certain level may indicate that the mask 14 is not properly secured to the face region 26 of the subject 24, or that a leak is present elsewhere in the ventilation system 10. Accordingly, in some embodiments the gauge may be used in coordination with a signal and/or alarm. The signal and/or alarm may provide an indication to a user that the ventilator system 10 is functioning properly or not. The signal and/or alarm may include visible markings on the gauge, one or more lights, a buzzer, a siren, or the like. For instance, in one embodiment, the gauge may have markings indicative of a high pressure (blockage), a safe pressure (proper flow), and/or a low pressure (leakage). In one embodiment, the pressure assessed by the gauge may be used to trigger the signal and/or alarms based on the status of the air/oxygen being administered.

In certain embodiments, the ventilation control system 21 includes a one or more manual valves. For instance, the ventilation control system 21 may include one or more valves having a lever, knob, dial, button, or the like that is actuated by a user. Actuation of the manual valve may operate the valve to increase or decrease one or more flow parameters of air/oxygen. Thus, a user can manually adjust the valve of the ventilation control system 21 to set one or more flow parameters of the ventilator system 10. In another embodiment, the ventilation control system 21 may include an automatic valve configured to regulate the flow parameters into specific default parameters. The automatic valve may enable adjustments of the flow parameters of the ventilator system 10 without a significant manual intervention. For example, in one embodiment, the system 10 may include a processor (e.g., an electrical circuit or mechanical circuit) configured to receive an input that is indicative of desired flow parameters. The processor may provide an output configured to operate the valve to maintain flow of the air/oxygen at or near the desired flow parameters. For instance, where a breath volume, maximum pressure limit, and respiratory-rate and flow rate is desired (e.g., an airflow profile that replicates one or more breathes) the automatic valve may open and close automatically to provide flow of air/oxygen to the subject 24 at the desired breath volume, maximum pressure limit, and respiratory-rate and flow rate.

The mask conduit 22 includes a path that routes air/oxygen from an outlet of the ventilator supply system 12 to an inlet of the mask 14. In an embodiment in which the ventilator supply system 12 and the mask 14 are disposed directly adjacent to one another, the mask conduit 22 may include the channel formed by the outlet of the ventilator supply system 12 and the inlet of the mask 14. In an embodiment in which the ventilator supply system 12 and the mask 14 are not disposed directly adjacent to one another and/or a substantial distance exists between the two, the mask conduit 22 may include a tube, pipe, or the like, that extends between the outlet of the ventilator supply system 12 and the inlet of the mask 14. For example, the mask conduit 22 may include a length of conduit extending from an outlet of ventilator supply system 12 to a collar of the mask 14. In one embodiment, the mask conduit 22 includes a flexible tube, such as plastic or corrugated tubing. In another embodiment, the mask conduit 22 includes a rigid component spanning the distance between the outlet of the ventilator supply system 12 and the inlet of the mask 14.

In some embodiments, the ventilator supply system 12 and the mask 14 may be removably coupled to one another and/or the mask conduit 22. Coupling between the mask conduit 22, the ventilator supply 12, and/or the mask 14 may be provided in various manners. In one embodiment, the connections include a threaded connection, an interference fit, locking detent features, an adhesive, or a combination thereof. Such a configuration may simplify the exchange of system components, such as the exchange of one mask 14 for another. For example, where the mask 14 is no longer suitable for service (e.g., the mask has a leak) or does not fit well onto the face region 26 of the subject 24, the interchangeable nature of the mask 14 may enable a user to remove the mask 14 and replace it with another mask.

In some embodiments, the mask conduit 22 and the mask 14 are integral with one another. For example, the mask 14 may include a hollow protrusion that extends from the mask 14 (e.g., a collar) that defines an inlet of the mask 14. The end of the collar opposite the mask 14 may be configured to mate with a complementary feature of the outlet of the ventilator system 12. Thus, at least a substantial portion of the mask conduit 22 is formed from the collar of the mask 14. In such an embodiment, the collar may enable coupling of a tube, connector, or other conduit to the mask 14. Further, the collar may provide an initial point of entry into the mask 14 for the air/oxygen and may route the air/oxygen from the inlet of the mask 14 into the concave region of the mask 14.

The interface between the mask 14 and the supply system 12 may optionally include one or more keying features. In such an embodiment, the keying features may ensure that the mask 14 is installed in correct orientation relative to the supply system 12 or that only certain masks 14 may be used in conjunction with the supply system 12. Also, a keying feature between the supply system 12 and the mask 14 could be required to allow air/oxygen flow through the system. This would ensure that the mask 14 is appropriately connected to the supply system 12 in order for air/oxygen flow to commence. In other words, without proper connection of the mask 14, and/or keying feature activation, air oxygen flow cannot begin. In some embodiments, air/oxygen flow may commence upon some form of activation, but air/oxygen flow will not commence without mask 14 attached. As discussed in more detail below, settings of the ventilator system 10 may be configured based on the size of the mask 14 determined by the assessment.

The mask 14 generally includes a device that routes air from the ventilator system 10 to the respiratory system of the subject 24. During use, the mask 14 may be placed over the face region 26 and held in place by a user. The user may press the mask 14 towards the face region 26 to promote a seal between mask 14 and the face region 26 of the subject 24. In certain embodiments, the mask 14 includes a ventilator mask that is secured to and placed over the face region 26 of the subject 24.

In one embodiment, the mask 14 includes a body having curvatures generally shaped to the subject's face region 26. For example, a body of the mask 14 may be formed from plastic that is molded to fit the contours of one or more types of face shapes. Generally, the mask 14 includes a concave shape that enables fitting the mask 14 over the nose and mouth of the subject 24. In some embodiments, the mask 14 includes rubber bands, elastic straps, or the like that can be disposed around the head and/or ears of the subject 24 and configured to secure the mask 14 to the subject 24 and further promote a seal of the mask 14 to the face region 26. In one embodiment, the mask 14 includes an additional sealing element, such as a foam or plastic ring, disposed along a sealing edge of the mask 14. The sealing element may promote the seal of the mask 14 to the face region 26 of the subject 24. As discussed above with regard to the mask conduit 22, the mask 14 may include a collar. The mask 14 may include a pressure relief valve as discussed previously. Pressure relief valve may also be a part of ventilation control system 21, or mask conduit 22.

In one embodiment, the mask 14 or another portion of the system 10 may include an exhalation port. The exhalation port may include a one-way valve that closes with the forward flow of air/oxygen during inspiration and opens as the air/oxygen moves in the opposite direction during the expiratory phase to expel expired air into the environment. The natural recoil of the chest walls generally provides the force to expel air during the expiratory phase.

In certain embodiments, the mask 14 may be configured in a size that will fit upon a selected range of sizes of human faces. The size of the mask 14 may affect how the mask secures and seals against the face region 26 of the subject 24. For example, if the mask 14 is too small, the sealing edge of the mask 14 may rest on the nose of the subject 24 and fail to provide an effective seal against other portions of the face, thereby allowing the air/oxygen to leak around the mask 14, as opposed to the air/oxygen being delivered to the lungs of the subject 24. If the mask 14 is too large, the sealing edge of the mask 14 may extend over the cheeks and chin of the subject 24, once again failing to provide an effective seal. However, where the mask 14 is fit properly to the face region 26 of the subject 24, the sealing edge of the mask 14 may provide an effective seal with the face region 26, thereby enabling the mask 14 to hold a sufficient pressure to route the air/oxygen into the lungs of the subject 24.

In some embodiments, the different sized mask 14 may be available to cover multiple size ranges of subjects 24. Each of these ranges may account for various shapes and sizes of faces. For example, in one embodiment, an adult-sized mask 14 is configured to fit a range of adult or large sized face regions 26, a child-sized mask 14 is configured to fit a range of child or medium sized face regions 26, and an infant-sized mask 14 is configured to fit a range of infant or small sized face regions 26. Thus, when operating the ventilator system 10, a user can assess the size of the subject 24 and/or the size of the face region 26 of the subject 24, select the mask 14 that appears to provide a sufficient fit and/or seal to the face region 26, couple the appropriate mask 14 to the ventilator supply system 12, secure the mask 14 to the face region 26, and proceed with providing air/oxygen to the subject 24 via the ventilation system 10. A sufficient fit may be assessed by observing whether or not a sealing edge of the mask 14 appears to contact at least a substantial portion of the face region 26, and observing the rise and fall of the subject's chest in relation to the inflow and outflow of air/oxygen as the ventilation supply system cycles.

Operation of the ventilator system 10 may include a series of steps to provide the flow of air/oxygen to the subject 24. For instance, in one embodiment, a user transports the ventilator system 10 to the subject 26, assesses the subjects face region 26, and selects the mask 14 that appears to fit snuggly around the nose and mouth of the subject 24 and that appears to provide a sufficient seal about the face region 26. The user may, then, couple the mask 14 to the ventilator supply system 12, secure the mask 14 to the face region 26 of the subject 24 and operate the ventilator system 10. The user might then initiate the flow of oxygen to initiate the function of ventilation control system 21. Operating the ventilator system 10 may include setting the flow parameters, such as the maximum pressure limit, breath volume, flow rate, and respiratory-rate of the air/oxygen. In an embodiment in which the ventilator system 10 is pre-configured to provide air/flow in accordance with a single set of flow parameters, however, the ventilator system 10 may not be conducive to use with a subject 26 requiring a different set of flow parameters. For example, where the ventilator system 10 is pre-configured to operate at a maximum pressure limit, breath volume and respiratory-rate, suitable for an adult, the ventilator system 10 may not be useful for administering artificial respiration to an infant. Further, even where a plurality of pre-determined flow parameters are available for the user to choose from, the user may not select the proper flow-parameters. For instance, the user may not know which settings to use or the user may select the incorrect setting inadvertently. Such a mistake could result in injury to the subject 24, or may result in insufficient or excessive air/oxygen pressure, breath volume and respiratory-rate delivered to the subject 24. As discussed in more detail below, certain embodiments include a system and method for automatically providing air/oxygen at pre-selected flow parameters (e.g., maximum pressure limit, breath volume, flow rate, and respiratory-rate) as a function of the characteristics (e.g., the size) of the mask 14 or any other airway device as discussed herein coupled to the ventilator supply system 10.

Figure 2:
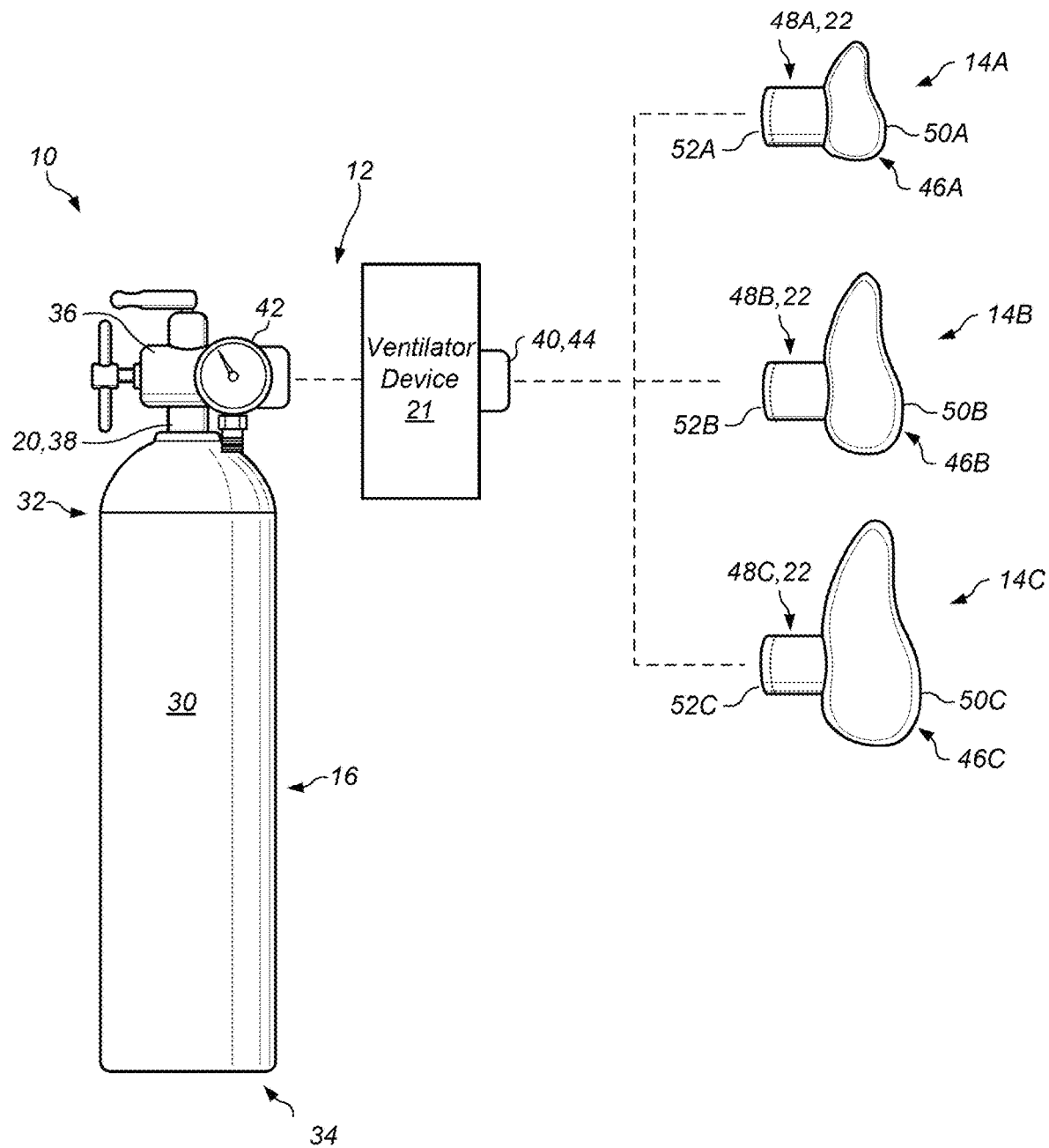
FIG. 2 is a schematic diagram that illustrates an embodiment of the ventilator system.

FIG. 2 is a schematic diagram that illustrates an embodiment of the ventilator system 10 in accordance with one or more embodiments. As depicted, the ventilator system 10 includes the ventilator supply system 12, and a plurality of masks 14A, 14B, and 14C. The ventilator supply system 12 includes the source 16, regulator 36 and ventilation control system 21. The source 16 includes a cylinder 30 having a first end 32 and a second end 34. In the illustrated embodiment, the supply conduit 20 includes a rigid structure that is integral with the regulator 36 and threaded into the first end 32 of the cylinder 30. The regulator 36 includes a regulator body having an inlet 38 integrated with the supply conduit 20. In the illustrated embodiment, the regulator 36 further includes a gauge 42 coupled to the body 36. On ventilation control system 21, supply outlet 40 includes a connector 44 that couples directly to the mask conduit 22. No tubing or additional conduit extends from the supply outlet 40.

In the illustrated embodiment each of the masks 14A, 14B, and 14C comprise a mask body 46A, 46B, and 46C, a mask inlet 48A, 48B, and 48C, and a sealing edge 50A, 50B, and 50C. No tubing or additional conduit extends from the inlets 48A, 48B, and 48C. The inlets 48A, 48B, and 48C each include connectors (e.g., collars) 52A, 52B, and 52C that are configured to couple directly to the connector 44 of the supply outlet 40.

The masks 14A, 14B, and 14C may include various types and/or shapes. In the illustrated embodiment, the body 46A of the first mask 14A has a small size, the body 46B of the second mask 14B has a medium size, and the body 46C of the third mask 14C has a large size. The small size mask 14A may be conducive for use with subjects 24 having smaller face regions 26, such as infants, and thus may be referred to as an infant-sized mask. The medium size mask 14B may be conducive for use with subjects 24 having medium sized face regions 26, such as children, and may be referred to as a child-sized mask. The large size mask 14C may be conducive for use with subjects 24 having larger sized face regions 26, such as adults, and may be referred to as an adult-sized mask. Each of the masks 14A, 14B, and 14C are coupleable to the ventilator supply system 12, as indicated by the dashed line between the connector 44 and each of the collars 52A, 52B, and 52C of the mask 14A, 14B, and 14C. Accordingly, a user may select one of the available masks 14A, 14B, and 14C, couple the selected mask 14A, 14B, or 14C to the ventilator supply system 12, secure the mask 14A, 14B, or 14C to the face region 26, and administer the air/oxygen to the subject 24.

In certain embodiments, the ventilator system 10 is configured to select operational parameters based on characteristics of the mask 14. For example, the ventilator system 10 may be configured to automatically provide air/oxygen in accordance with a pre-selected set of flow parameters based on one more characteristics of the mask 14 coupled to the ventilator supply system 12. In one such embodiment, the ventilator system 10 provides air/oxygen at a pre-selected maximum pressure limit, breath volume, flow rate and/or respiratory-rate based on the size of the mask 14 coupled to the ventilator supply system 12. The pre-selected flow parameters may include a predetermined set of flow parameter values that are associated with each size of the mask 14. For example, in an embodiment in which the infant-size mask 14A is coupled to the ventilator supply system 12, the ventilator system 10 may be automatically configured to provide air/oxygen in accordance with one or more pre-selected flow parameters that are appropriate for artificial respiration for an infant. In an embodiment in which the child-size mask 14B is coupled to the ventilator supply system 12, the ventilator system 10 may be automatically configured to provide air/oxygen flow in accordance with one or more pre-selected flow parameters that are appropriate for artificial respiration for a child. In an embodiment in which the adult-size mask 14C is coupled to the ventilator supply system 12, the ventilator system 10 may be automatically configured to provide air/oxygen flow in accordance with one or more pre-selected flow parameters that are appropriate for artificial respiration for an adult. Other embodiments may include any number of sizes and types of mask and/or sets of pre-selected flow parameters. For example, additional sizes and associated flow parameters may be available for males and females. Further, two mask 14 may have the same size, but may be associate with varying flow parameters. For example, one size of mask may be designated as a high-pressure type mask that is associated with pre-selected flow parameters having a higher maximum pressure, or a low-pressure type mask that is associated with pre-selected flow parameters having a lower maximum pressure. Further, multiple mask sizes may be associated with a set of flow parameters. For example, ventilation parameters appropriate for children may be engaged by use of toddler sized mask or a larger child sized mask.

Table 1 provides an exemplary listing of flow parameters for an adult, a child and an infant. The information in this table is derived from recommendations provided by the American Heart Association (AHA). The AHA generally assumes that an infant includes a baby up to one year of age, a child is from one year to eight years of age, and an adult is over eight year of age. The values listed in Table 1 are based on recommendations of the AHA although each value for infants and children may not be explicitly set forth by the AHA. For example, the AHA does not provide a tidal volume, but instead recommends a tidal volume sufficient for visible chest rise. For the purposes of one embodiment based on observation and clinical experience, the breath volume ($V_T$) of 100 cc for an infant is based on an approximate infant weight of 10 kg and a ratio of 10 cubic centimeters (cc) per kilogram (kg). Similarly, the breath volume of 300 cc for a child is based on an approximate child weight of 30 kg and a ratio of 10 cc/kg. The breath volume for an adult of 600 cc is based on the recommended range of 500-600 cc provided by the AHA. It will be appreciated that these values are exemplary of one embodiment of the system and may be modified based on the application and/or based on revised or other relevant standards, such as those provided by the AHA.

TABLE 1

| Flow/Respiratory Parameters | | | | | |
|---|---|---|---|---|---|
| Breath Volume ($V_T$) (cc) | Respiratory Rate (RR) (breaths/min) | Peak Pressure $P_{IP}$ (maximum pressure limit) (cmH$_2$O) | I:E Ratio | Flow Rate (L/min) | Mask Size |
| Adult 600 | 10 | 40 | 1:5 | 6 | Adult |
| Child 300 | 20 | 20 | 1:2 | 6 | Child |
| Infant 100 | 30 | 20 | 1:1 | 3 | Infant |

In accordance with an embodiment based on the parameters listed in Table 1, in one embodiment, the ventilator system 10 is automatically configured to provide air/oxygen having a maximum pressure limit of 20 centimeters of water (cmH$_2$O), a breath volume of 100 cubic centimeters (cc), a respiratory-rate of 30 breaths/minute, an I:E ratio of 1:1, and/or a flow rate of 3 liters per minute (L/min) when the infant-size mask 14A is coupled to the ventilator supply system 12. Flow rates listed are exemplary only. Actual oxygen flow rates may be higher or lower depending on engineering needs and/or regulatory issues. In one embodiment, the ventilator system 10 is automatically configured to provide air/oxygen having a maximum pressure limit of 20 cmH$_2$O, a breath volume of 300 cc, a respiratory-rate of 20 breaths/min, an I:E ratio of 1:2, and/or a flow rate of 6 L/min, when the child-size mask 14B is coupled to the ventilator supply system 12. In one embodiment the ventilator system 10 is automatically configured to provide air/oxygen having a maximum pressure limit of 40 cmH$_2$O, a breath volume of 600 cc, a respiratory-rate of 10 breaths/min, an I:E ratio of 1:5, and/or a flow rate of 6 L/min when the adult-size mask 14C is coupled to the ventilator supply system 12. The I:E ratio is a ratio of the time of the inspiratory phase to the expiratory phase of the respiratory cycle. The AHA recommends that each breath be given over one second (e.g., on second for the inspiratory phase). For example, based on the adult respiratory parameters of Table 1, the I:E ratio of 1:5 is determined by 10 breaths per minute (e.g., six seconds per breath), where one second is needed for the inspiratory phase and the other five seconds are used for the expiratory phase. In other embodiments, one or more of the pre-selected flow parameters includes a range (e.g., a maximum and minimum value), as opposed to a single target value. Further, in other embodiment, the ventilation technique may be varied. For example, one embodiment may include pressure-controlled ventilation. For example, the inspiratory phase of the breath may be given until a certain pressure is reached, and the expiratory phase may, then, begin.

Further, one embodiment may provide for a low flow of oxygen during the expiratory phase of the respiratory cycle to assist in the dilution and washout of expired carbon dioxide from the mask. This may decrease the re-breathing of carbon dioxide that may remain in the mask from the previously expired breath.

Figure 3A:
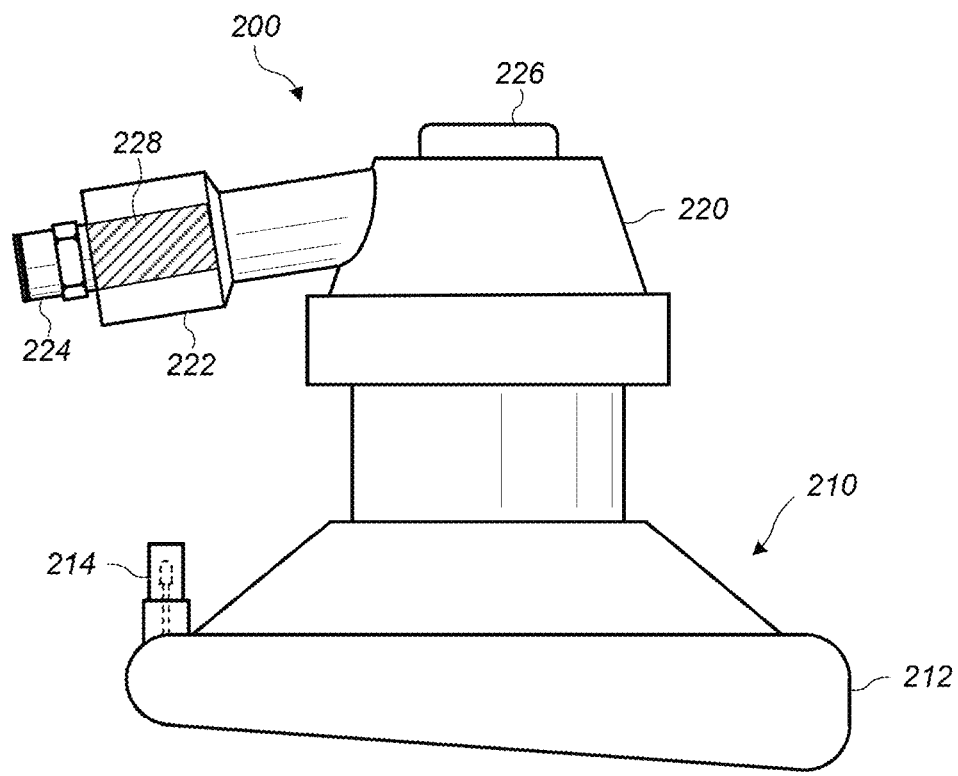
FIG. 3A depicts an embodiment of a mask.

FIG. 3A depicts an embodiment of a mask 200. Mask 200 includes a mask body 210 and a mask inlet port 220. Mask body 210 includes a sealing edge 212 which can be placed against the subjects face and create a substantially airtight seal over the subject's nose and mouth. In the depicted embodiment, sealing edge 212 is in the form of an airtight container which can be inflated using inflation port 214. It should be understood, however, that sealing edge may be formed from any material that can form of a substantially airtight seal when placed against a subjects face.

Mask inlet port 220 includes an inlet conduit 222 which is used to couple the mask to the outlet conduit 22 of the ventilation control system 21. Inlet conduit 222 includes a connector 224 which is designed to allow easy and quick coupling of mask 200 to conduit 22. In some embodiments, connector 224 is one part of a quick connect/disconnect coupling system. Quick connect/disconnect systems for coupling conduits which transfer pressurized gases are well known. Inlet port 220 also includes a pressure relief valve 226. During use, if the pressure inside the mask reaches a predetermined maximum pressure, pressure release valve 226 opens, reducing the pressure inside mask body 210.

Figure 3B:
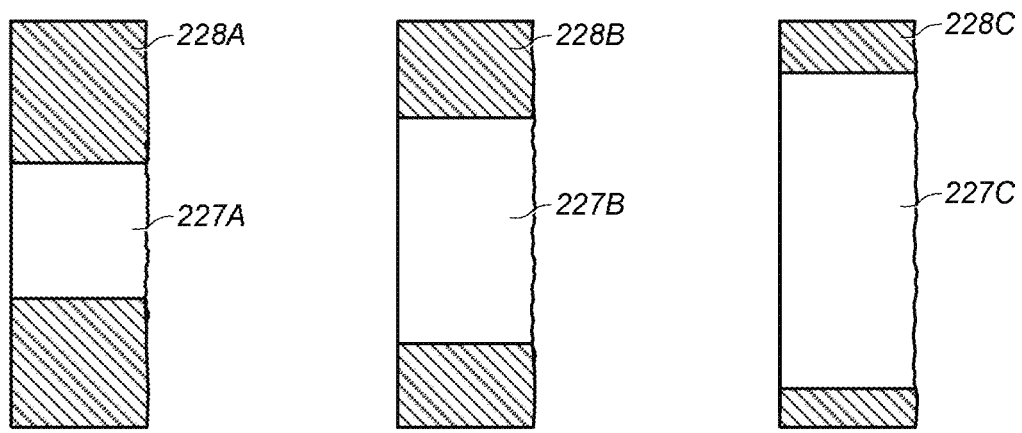
FIG. 3B depicts exemplary flow gas restrictors.

Mask inlet port also includes a gas flow restrictor 228. Gas flow restrictor creates an increase in pressure in the ventilation control system by providing a reduced diameter of flow path of air/oxygen into inlet port 220. The increased pressure is proportional to the diameter of a passageway 227 which passes through gas flow restrictor 228. A larger passageway through gas flow restrictor 228 will create less pressure increase than a smaller passageway. In one embodiment, different gas flow restrictors are used in different mask types. Exemplary gas flow restrictors 228A, 228B, and 228C are depicted in FIG. 3B. In one embodiment, gas flow restrictor 228A may be used in an infant-size mask, gas flow restrictor 228B may be used in a child-size mask, and gas-flow restrictor 228C may be used in an adult-size mask. During use, each of flow restrictors 228A, 228B, and 228C create different pressure increases. Based on the measured pressure increase, the ventilator system 12 may be automatically configured to output air/oxygen having flow parameters in accordance with pre-selected flow parameters that are associated with the size, type and/or other characteristics of the mask 14.

Figure 4A:
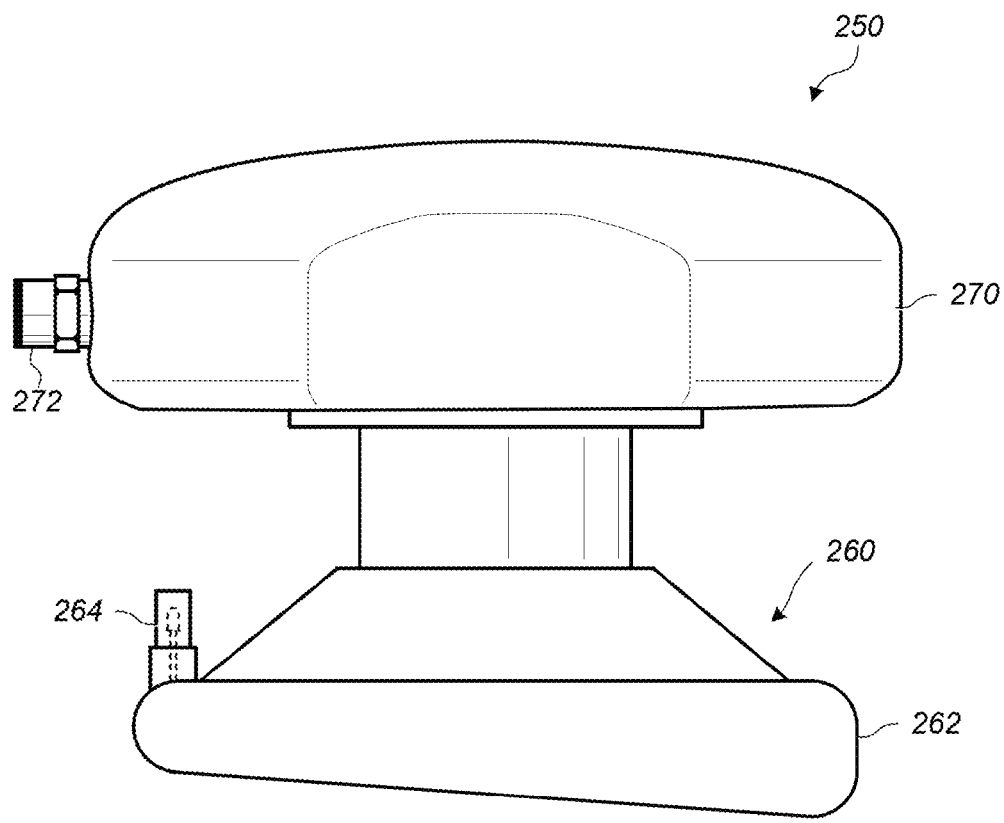
FIGS. 4A-4B depict an alternate embodiment of a mask.
Figure 4B:
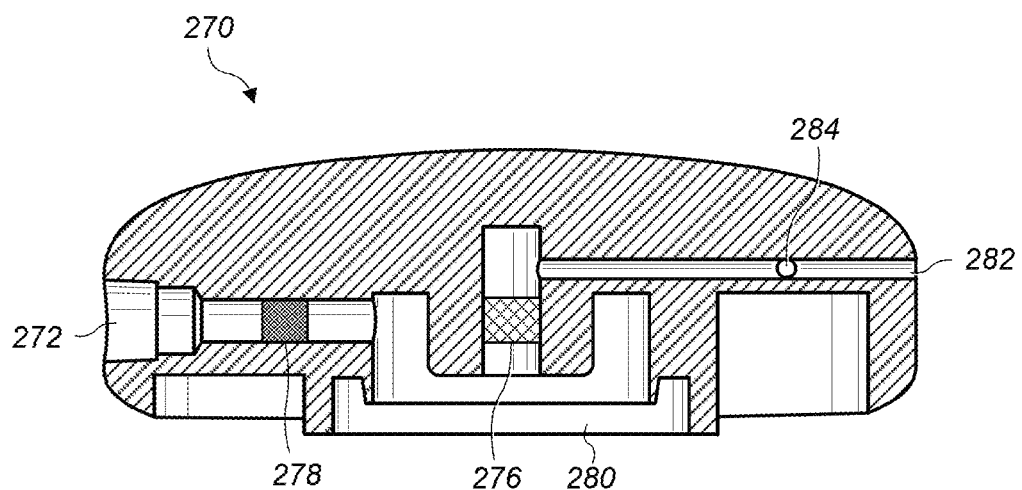

FIGS. 4A-4B depict an alternate embodiment of a mask 250. Mask 250 includes a mask body 260 and a mask inlet port 270. Mask body 260 includes a sealing edge 262 which can be placed against the subjects face and create a substantially airtight seal over the subject's nose and mouth. In the depicted embodiment, sealing edge 262 is in the form of an airtight container which can be inflated using inflation port 264. It should be understood, however, that sealing edge may be formed from any material that can form of a substantially airtight seal when placed against a subjects face.

Mask inlet port 270, in some embodiments, is composed of an ergonomically molded enclosure/case such that a user can easily grasp the mask to position the mask on the face of the subject 24 during use. In some embodiments, mask inlet port may have a predetermined color based on the size or intended use of mask 250. A cross-sectional view of inlet port 270 is depicted in FIG. 4B. Mask inlet port 270 includes an inlet connector 272 which is used to couple the mask to the outlet conduit 22 of the ventilation control system 21. Inlet connector 272 is designed to allow easy and quick coupling of mask 250 to conduit 22. In some embodiments, connector 272 is one part of a quick connect/disconnect coupling system. Inlet port 270 also includes a pressure relief valve 276. During use, if the pressure inside the mask reaches a predetermined maximum pressure, pressure release valve 276 opens, reducing the pressure inside mask body 260.

Mask inlet port also includes a gas flow restrictor 278. Gas flow restrictor creates an increase in pressure in the ventilation control system by providing a reduced diameter of flow path of air/oxygen into inlet port 270. The increased pressure is proportional to the diameter of a passageway which passes through gas flow restrictor 278. As previously discussed a larger passageway through gas flow restrictor 278 will create less pressure increase than a smaller passageway. Exemplary gas flow restrictors 228A, 228B, and 228C are depicted in FIG. 3B.

During use, air/oxygen enters inlet port 270 through inlet connector 272. The air/oxygen is directed to gas flow restrictor 278 which increases the pressure in the inlet connector and the conduit 22 leading to the ventilation control system 21. Based on the detected pressure increase, ventilation control system 21 begins delivering pulses of air/oxygen to the mask according to predetermined parameters which are specific for the mask being used. The air/oxygen passes through flow restrictor 278 and through mask body inlet conduit 280 to mask body 260. The air/oxygen is delivered to mask body 260 at a pressure sufficient to inflate the lungs of the subject. If the pressure inside mask body 260 increases beyond a predetermined amount, the air/oxygen is released form mask body 260 through pressure release valve 276. Air/oxygen released through pressure release valve 276 is released out of inlet port 270 through conduits 282 and 284 which allow the pressurized air/oxygen to escape mask body 260.

Figure 5:
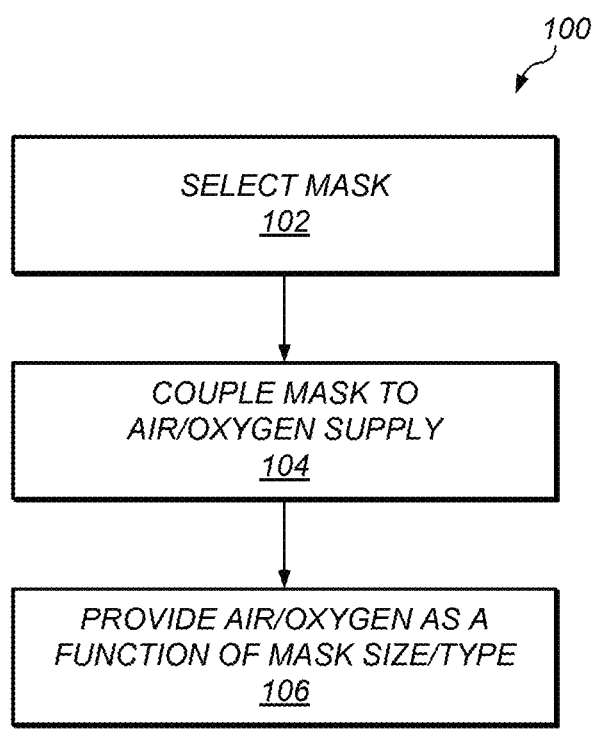
FIG. 5 is a flowchart that illustrates a method of operating a ventilator system.

FIG. 5 is a flowchart that illustrates a method 100 of operating the ventilator system 10 in accordance with one or more embodiments of the present technique. The method 100 generally includes automatically providing air/oxygen at pre-selected flow parameters (e.g., maximum pressure limit, breath volume, flow rate and respiratory-rate) as a function of characteristics (e.g., a size and/or type) of a mask 14 coupled to the air/oxygen ventilator system 10. In one embodiment, the method 100 includes selecting a mask, as depicted at block 102. Selecting a mask (block 102) may include a user selecting one mask 14 from a plurality of masks 14A, 14B, or 14C that are available for use with the ventilator system 10. For example, in one embodiment, the plurality of available masks available for use may include three masks 14A, 14B, and 14C of varying sizes. The three masks 14 may include one mask sized to fit an infant's face 14A, one mask sized to fit a child's face 14B, and one mask sized to fit an adult's face 14C. In such an embodiment, selecting the mask (block 102) may include the user assessing the size of the subject 24, estimating which mask 14A, 14B, or 14C may be of the appropriate size, holding the mask 14A, 14B, or 14C to the subject's face region 26 to ensure a proper fit, and repeating the procedure until the user determines which mask 14A, 14B, or 14C appears to provide the best fit and seal to the subject's face region 26.

In one embodiment, the method 100 also includes coupling the mask to an air/oxygen supply, as depicted at block 104. In one embodiment, this may include the user physically coupling an inlet of the mask 14 to an outlet of the ventilator supply system 12. For example, the mask 14 may be coupled directly to a connector 44 of the ventilator supply system 12 or the mask 14 may be coupled to a mask conduit 22, such as flexible tubing that extends between the inlet 48A, 48B, or 48C of the mask 14 and the outlet 40 of the ventilator supply system 12.

As depicted at block 106, the method 100 may includes providing air/oxygen flow as a function of the mask type and/or size. For instance, in one embodiment, providing air/oxygen flow as a function of the mask type and/or size (block 106) includes assessing the size of the mask 14 that is coupled to the air/oxygen supply system 12. Assessing the size of the mask may include assessing a signal that is indicative of the mask coupled to the ventilator supply system 12 (e.g., a signal proportional to the pressure increase which occurs when air/oxygen is provided to the mask).

Further providing air/oxygen flow as a function of the mask type and/or size (block 106) may include providing air/oxygen flow with flow parameters associated with the type/size of the mask 14 coupled to the ventilator supply 12. For example, where the a ventilator supply system is configured to provide air/oxygen at a pre-selected maximum pressure limit, breath volume, flow rate and/or respiratory-rate based on the size of the mask 14 coupled to the supply system 12, the air/oxygen may be routed from the ventilator system 10 in accordance with a set of flow parameters associated with the size of the mask 14.

Various elements and aspects of the method 100 described herein can be combined, reversed, or omitted. For example, with respect to providing air/oxygen as a function of mask type/size, the method may include only this step, and it not dependent on the steps of selecting a mask (block 102) and coupling the mask to the air/oxygen supply (block 104), that may be performed by a user.

In some embodiments, the ventilator system 10 may include a port/valve that facilitates the inhalation of air/oxygen from the source 16 and the exhalation of air/oxygen to another location, such as the surrounding atmosphere. Such an embodiment may facilitate the delivery of pressurized air/oxygen to the subject 24, while enabling the subject 24 to exhale air/oxygen to the relatively unpressurized atmosphere. Thus, pressurized air/oxygen may be forced into the lungs of the subject 24 via the mask 14, and the restoring force of the expanded lungs of the subject 24 may be capable of providing enough pressure to force the air/oxygen to the atmosphere via the port/valve, thereby evacuating the air/oxygen from the lungs, without removing the mask 14 from the subject 24. During use, cycling of pressure of air/oxygen being provided to the port/valve may regulate the inspiration time and the expiration time. For example, when pressurized air/oxygen is provided from the source 16 to the port/valve, air/oxygen may be directed into the lungs of the subject 24 via mask 14, while the exit of the pressurized air/oxygen to the atmosphere is inhibited. Further, when the pressure of the air/oxygen provided from the source 16 is reduced or eliminated, the port/valve may direct air/oxygen (e.g., exhaled air/oxygen) to the surrounding atmosphere, while inhibiting the upstream flow of the air/oxygen toward the source 16. In some embodiments, the operation of the port/valve is dependent on the relative pressure of the air/oxygen being provided from the source 16 and the pressure of the air/oxygen provided to the mask 14 from the subject 24 (e.g., the pressure of the air/oxygen contained in and/or exhaled from the lungs of the subject 24). For example, where the pressure of the air/oxygen provided from the source 16 is greater than the opposing pressure of the air/oxygen generated by the restoring force of the expanded lungs of the subject 24, the port/valve may remain in a first (opened) position to facilitate the flow of air/oxygen from the source 16 into the lungs of the subject via the mask 14 and the port/valve, and to inhibit the flow of air/oxygen to the surrounding atmosphere via the port/valve. Where the pressure of the air/oxygen provided from the source 16 is less than the opposing pressure of the air/oxygen generated by the restoring force of the expanded lungs of the subject, the port/valve may remain in a second (closed) position to facilitate the exhalation and flow of air/oxygen from the lungs of the subject 24 to the surrounding atmosphere via the mask 14 and the port/valve, and to inhibit the flow upstream toward the source 16 via the port/valve.

Ventilator system 10 may be suited for configuration as a portable ventilation system 10. For instance, each of the components of the ventilation system 10 can be combined into a single-portable unit that can be stored and activated at or near the location of an emergency. Such a portable unit, may be suitable for use in homes, schools, industrial settings, hotels, commercial office buildings, commercial aircraft, and the like, where having a conveniently placed ventilator system 12 may be beneficial to providing assistance to those performing CPR.

In one embodiment, such as that depicted in FIG. 2, the cylinder 30 may include a shape conducive to being handled by a user. For example, the cylinder 30 may include a diameter, shape, grip, handle, or the like, such that a user can grasp the ventilator system 10 by the cylinder 30. Such a configuration may assist a user's dexterity in handling the ventilator system 10 before, during and after the administration of CPR to the subject 24. For example, a user may hold the ventilator system 10 and mask 14 secure to the face region 26 of the subject 24 with one hand while checking the pulse of the subject 24 with the other hand. Other embodiments may include features such as wheels or a carrying strap conducive to transport and handling of the system 10.

Figure 6E:
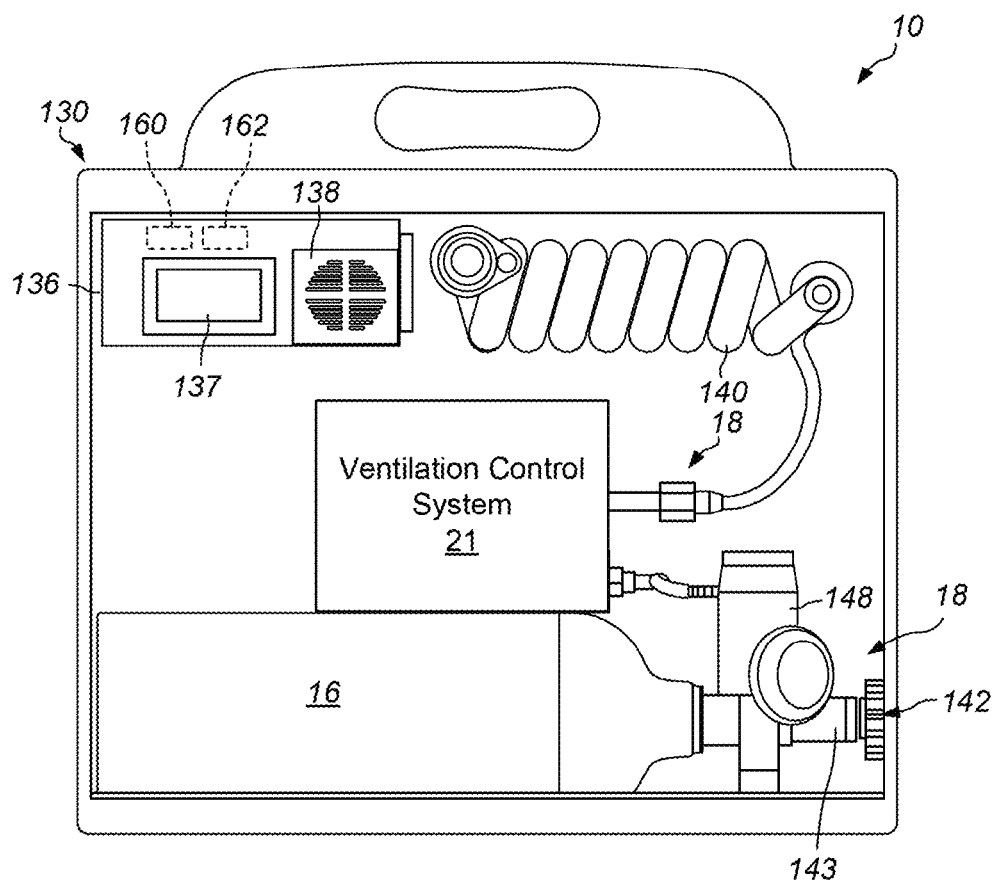

FIGS. 6A-6E include illustrations of a portable ventilator system 10 in accordance with embodiments of the present technique. In the illustrated embodiments, ventilator system 10 includes an enclosure 130 having a lid 132, an internal cover 134, masks 14A, 14B, 14C provided in respective cradles of the internal cover 134, a communications device 136 including a display 137 and a microphone/speaker 138, a flexible respirator hose/conduit 140, a case plug 142, and a ratchet arm 144. As illustrated in FIG. 6E having internal cover 134 removed, portable ventilator system 10 also includes, internally, an air/oxygen source cylinder 16, an air regulation system 18 including a regulator 148, and a ventilation control system 21.

Enclosure 130 may include a case that protects and organizes the components of the portable ventilator system 10. For example, the enclosure may include a plastic or metal case that is of suitable size to be readily transported by a user, such as a "Pelican" case manufactured by Pelican-Case, having headquarters in San Antonio, Tex. In some embodiments, opening of the enclosure 130 may provide activation of one or more functions. For example, opening of the lid 132 may cause the ratchet arm 144 to engage and rotate the case plug 142, which is coupled to valve 143, thereby rotating a valve of the air/oxygen source into an opened/activated position that facilitates the delivery of air/oxygen from the source 16.

Further, it is anticipated that dialing a 911 operator may be helpful, thus, certain embodiments may include a telephonic device, such as a cell phone, or other communications device, that may enable a user to make a call to 911 in conjunction with use of the ventilator system 10. For example, in one embodiment, a button, voice activated, or user activated switch may be located on the ventilator system 10 such that a user may place a call to a 911 operator. In one embodiment, the ventilator system 10 may be configured to only place calls to 911, and not receive 911 calls. Accordingly, there may be no additional access fee required as connections to 911 may not be charged a fee and operation of such a uni-directional cellular may not require a monthly access fee. One embodiment may include the ventilator system 10 configured to provide for wireless internet access, satellite phone access, access to an operator, access to an emergency room physician, access to a CPR support center, or the like.

In some embodiments the (portable) ventilator system 10 includes a communications device that, during use, automatically contacts an emergency response entity in response to activation of the ventilator system 10. An emergency response entity may include paramedics, a fire department, a police department, local security personnel, local medical personnel (e.g., a nurse station), or the like. In some embodiments, automatically contacting an emergency response entity comprises notifying an emergency responder of activation of the portable ventilator system. For example, the communication device 136 of ventilator system 10 may place a call to an emergency responder (e.g., call "911"), may send a textual message to an emergency responder, or a similar alert. In some embodiments, activation of the portable ventilator system includes removing the ventilator system 10 from a storage location (e.g., removing the system from a case, or rack), opening the enclosure 130 of the ventilator system 10, coupling of a ventilator mask to an air/oxygen source and/or an air/oxygen regulator system of the ventilator system 10, initiation of air/oxygen flow through at least a portion of the ventilator system 10, manual activation of an input of the ventilator system 10 by a user (e.g., pressing a power/start/alert/activation button or initiating air/oxygen flow from source 16), or the like. In some embodiments, the communications device 136 may be manually activated by a user to communicate with an emergency response entity. In some embodiments, communications device 136 may be activated automatically and/or manually. For example, the communications device 136 may initiate contact of an emergency response entity automatically upon activation and/or in response to a user manually requesting that such a contact/communication be established.

In some embodiments, the communication device 136 may be used to communicate instructions to a user. In one embodiment, audible instructions may be provide to the user via speaker 138. For example, after contacting an emergency response entity, a representative (e.g., a 911 dispatcher) may provide instructions describing how to provide CPR to the subject using the ventilator system 10. In some embodiments, pre-stored audible instructions may be provided to the user via the speaker 138 upon activation of the ventilator system 10 and/or a manual request from a user for instructions (e.g., pressing a button to request the audible instructions). In one embodiment, visual instructions may be provided to a user via the display 137. For example, upon activation of the ventilator system 10, textual, graphical, and/or animated instructions may be displayed to the user via the display 137. This may include activating lights (e.g., LEDs) or a displayed textual description to indicate the status of the ventilator system 10 (e.g., active, functioning properly, not functioning properly, operating in infant/child/adult mode), what mask to choose, how to couple the mask to the subject, etc. In some embodiments, graphical animations of how to use the ventilator system 10 may be provided via the display 137.

In some embodiments, the communications device 136 may provide for two-way communication between the emergency response entity and a user of the portable ventilator system. For example, a user may provide input (e.g., press a button or speak into the microphone 138) and may receive feedback from an emergency responder (e.g., audible instructions via the speaker 138 or textual/graphical instructions via the display 137).

In certain embodiments, ventilator system 10 may include a processor 160 (a controller) configured to implement certain routines to provide various functions described herein. In some embodiments, a ventilator system 10 may include a non-transitory computer readable storage medium 162 (e.g., a floppy disk, random access memory (RAM), read only memory (ROM), hard drive, flash memory, or the like) having program instruction stored thereon. The program instructions may be executable by a processor to implement various functions described herein. For example, the program instructions may be executed to provide displayed or audible instructions for using the ventilator system 10, to contact an emergency response entity, or the like.

In certain embodiments, one or more portions of the system may be provided at or near the mask. For example, the system may include a ventilator device coupled directly to the mask. The ventilator device may be provided at or near an input of the mask and coupled to the regulator and the source via a conduit. The ventilator device may include an ergonomically molded enclosure/handle such that a user can easily grasp the ventilator device to position the mask on the face of the subject during use.

Although a portable configuration may be advantageous in certain scenarios, the ventilator system 10 may also include a generally non-portable configuration. For example, where it is anticipated that the ventilation system 10 may be used for an extended period of time (e.g., an hour or more), the source 16 may be increased in size or supplemented by another supply, such as a large cylinder, a second small cylinder, or stand-alone oxygen supply unit generally available in a hospital or similar medical facility or aircraft, fire truck, ambulance or other emergency vehicle. Such an embodiment may be employed within a health care facility to ensure that flow parameters are selected based on the mask coupled to the ventilator system 10, and ensure that even trained professionals do not inadvertently select inappropriate flow parameters.

Although certain embodiments have been discussed in detail, other embodiments of the system 10 are within the scope of this disclosure. For example, although much of the disclosure has considered the type and/or size of a mask, other embodiments may consider the type and/or size of another air delivery device, such as an endotracheal tube, king airway, laryngeal mask airway, or other device configured to route air/oxygen to the lungs of a subject. Further, while the current description focuses on a singular ventilation control system with a plurality of preset ventilator parameters which are selected based on the particular mask in use, another embodiment may include a plurality of ventilation control system/mask combination units where the mask and ventilation control system exist as a single unit. In this embodiment, the system would include three or more separate ventilation control system/mask combinations with the particular mask corresponding to the airflow characteristics which that particular ventilation control system is preset to deliver. To use this particular embodiment, the user would, instead of selecting the desired mask and attaching it to the ventilation control system, select from a plurality of ventilation control system/mask combination units, the mask size corresponding to the parameters which are preset into the device. Further, the system 10 has been discussed in the context of a ventilator system; however, other embodiments may include similar forms of air/oxygen delivery devices, such as a respirator.

In other embodiments, the ventilator system 10 may incorporate and/or be combined with various medical devices. For example, in one embodiment, the ventilator system 10 may be provided in conjunction with and/or include a defibrillator. As discussed above, when air/oxygen is delivered via the ventilator supply system, and is used to assist respiration and oxygenation, the defibrillator may, then, be employed in an attempt to correct lethal cardiac electrical activity. For instance, CPR may be performed prior to administering an electric shock to the heart via the defibrillator, as this may increase the likelihood of defibrillation success, and improve the chance for victim survival. The ventilator system 10 may include a carbon dioxide detector in one embodiment. For example, a carbon dioxide detector cartridge may be placed in the system and configured to assist in the detection of the presence of carbon dioxide and confirm air movement from the patient. Further, embodiments may include airway devices such as oral airways, nasal trumpets, laryngeal mask airways and CPR prompts (e.g., audible beep to prompt when to do compressions), or Broslow charts. Further, embodiments may include endotracheal tube, laryngeal mask airway, king airway or other advanced airway device connections having a keying feature similar to those described herein. Such embodiments may enable use of the system with endotracheal tubes and/or masks, and or other airway devices.

The ventilator system 10 may include medications provided with the unit that could be administered to the subject 24. For example, the ventilator system 10 may include a compartment configured to contain Epinephrine for allergic reactions or asthmatic emergencies. These could be used only under stringent guidelines, and/or specific direction from one licensed or allowed to prescribe or administer drugs.

Figure 7:
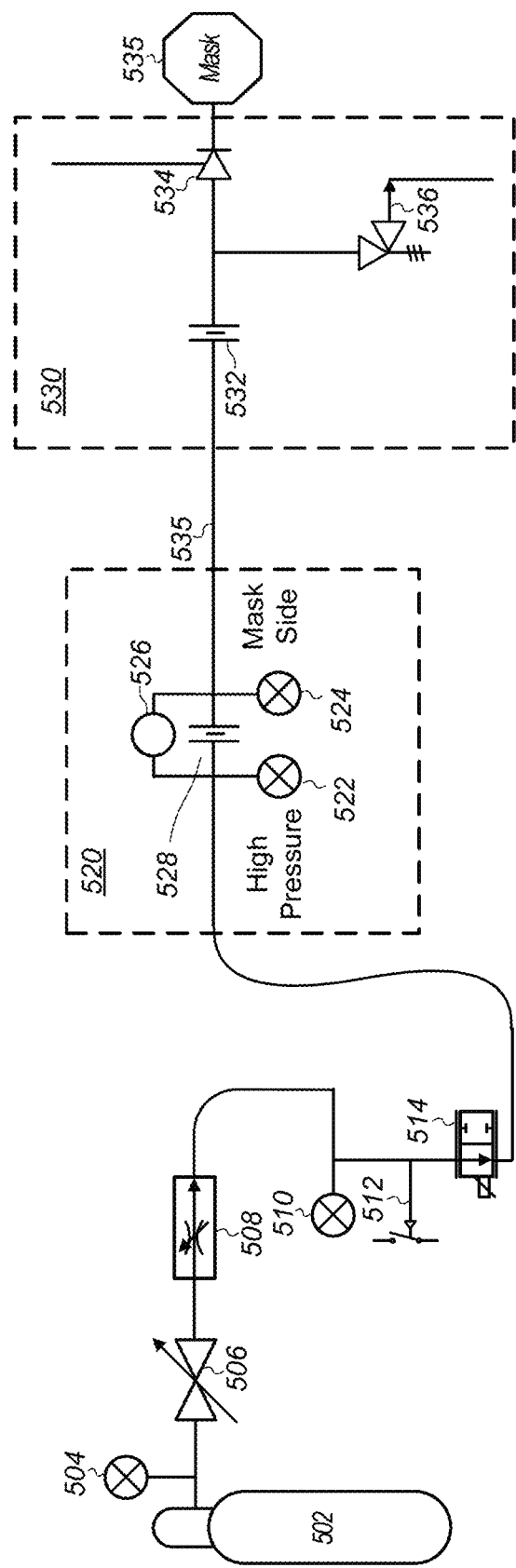
FIG. 7 depicts a schematic diagram of a ventilator system.

FIG. 7 depicts a schematic diagram of a ventilator system 500. Ventilator system 500 includes an air/oxygen supply source 502 which provides air/oxygen to the system. A pressure gauge 504 is coupled to the air/oxygen supply source 502. Pressure gauge 502 indicates the pressure of the gas (and thus the amount of gas) in the air/oxygen supply source. Air/oxygen supply source 502 is coupled to supply regulator 508 which controls the release of air/oxygen from the air/oxygen supply source. In an embodiment, supply regulator 508 is configured to release gas from the air/oxygen supply source at a predetermined pressure (e.g., 50 psi). This ensures that a constant supply of gas at a known pressure is received from air/oxygen supply source 502.

Gas pressure gauge 510 measures the pressure of the incoming gas. The pressure of the incoming gas is conveyed to a controller (not shown) which can adjust the operating parameters of the ventilator system based on the detected pressure. The gas is then conveyed to a pressure actuated switch 512. Pressure actuated switch 512 allows the system to be turned on when pressurized gas is received by the switch. The use of a pressure activated switch allows the system to be activated by opening the supply regulator 508. In some embodiments, as described above, supply regulator may be opened when a case containing the ventilator system is opened.

Once the system is activated, an electronic proportional valve 514 controls the delivery of air/oxygen to the system to create the appropriate respiration pattern. The proportional valve, in one embodiment, includes a plunger which is electronically actuated to move the plunger in an analog fashion within the valve. This allows the controller to vary the amount of gas passing through the valve in order to create the desired respirations.

As discussed previously, a ventilator system may rely on a change in pressure to determine the type of mask being applied to the subject. In one embodiment, a pressure differential system 520 is used to provide feedback to the controller. In an embodiment, pressure differential system includes a first (high pressure side) pressure sensor 522 and a second (mask side) pressure sensor 524 and a flow rate sensor 528. A pressure gauge 526 is coupled to the first and second pressure sensors and determines the pressure differential across the flow rate sensor.

During use the mask side of the pressure differential system varies as the air/oxygen is sent into the patient. The differences in pressure can be used to control the amount of air/oxygen delivered to the mask. In an embodiment, the pressure differential detected by pressure gauge 528 is used to control the proportional valve 514 such that the appropriate amount of air/oxygen enters the system. The air/oxygen passes out of pressure differential system into conduit 525 for delivery of air/oxygen to a mask 535.

As discussed above, the identification of mask 535 is automatically performed by the ventilation system based on a change in pressure. In an embodiment, inlet port 530 of mask 535 includes gas flow restrictor 532. During use, when mask 535 is coupled to conduit 525, the gas flow restrictor causes the pressure in the conduit, and thus on the mask side of the pressure differential system increase. The amount of the pressure increase is proportional to the gas flow restrictor 532 that is coupled to the mask, and thus, as described earlier, can be used by the system controller to identify the mask being applied to the subject. Inlet port 530 also includes a vented check valve 534 which prevents backflow of air/oxygen after the gas is delivered to the patient. Inlet port also includes pressure relief valve 536 which is used to release gases from the mask 535 if the pressure inside the mask exceeds a predetermined pressure.

In an embodiment, a ventilation control system 21 includes the following components: incoming gas pressure gauge 510; pressure actuated switch 512; proportional valve 514; and pressure differential system 520. All of these components, as well as the electronic controller, may be enclosed in a case and disposed in the ventilator system as shown, for example, in FIG. 6E. An embodiment of the ventilation control system is depicted in FIGS. 8 and 9.

Figure 8:
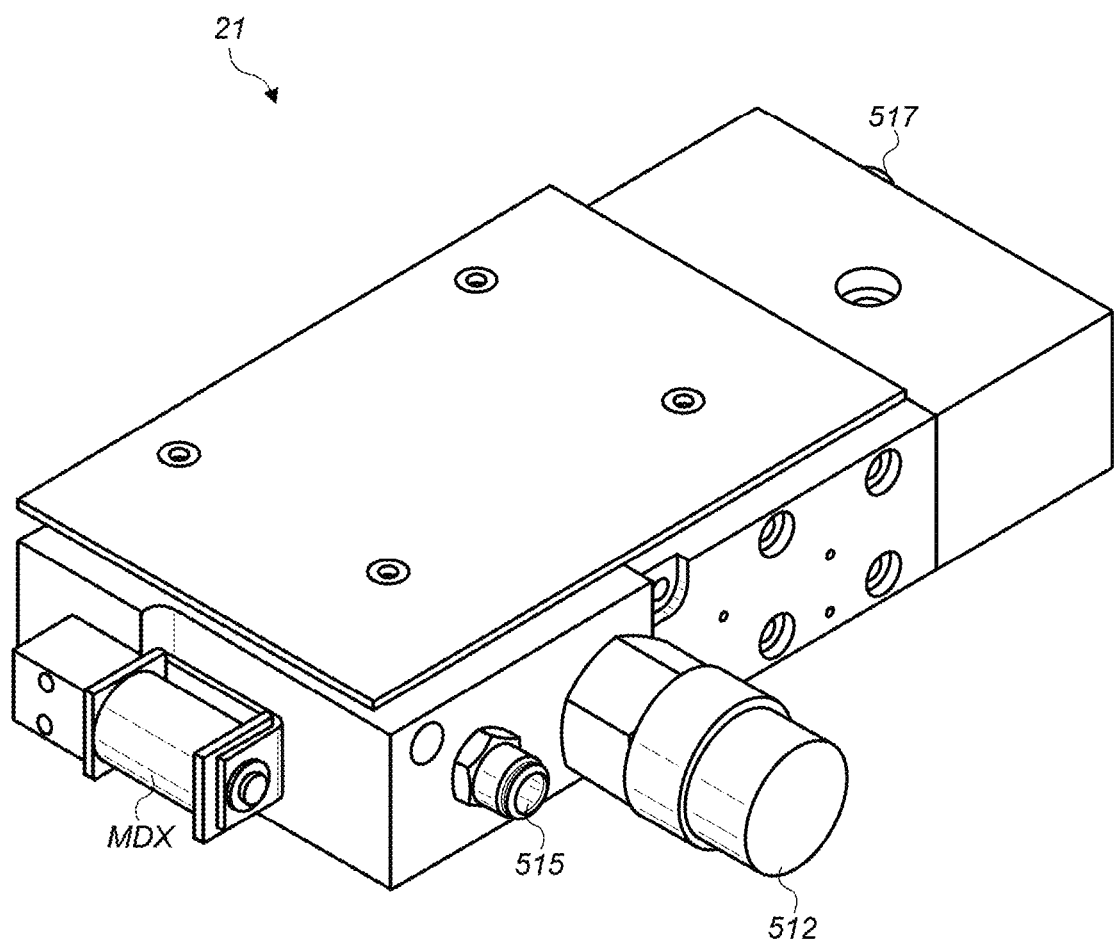
FIG. 8 depicts an exterior perspective view of a ventilation control system.

FIG. 8 depicts an exterior perspective view of ventilation control system 21. Visible from the exterior of the ventilation control system are; gas inlet 515; pressure actuated switch 512; pressure gauge 510; proportional valve 514; and outlet port 517.

Figure 9:
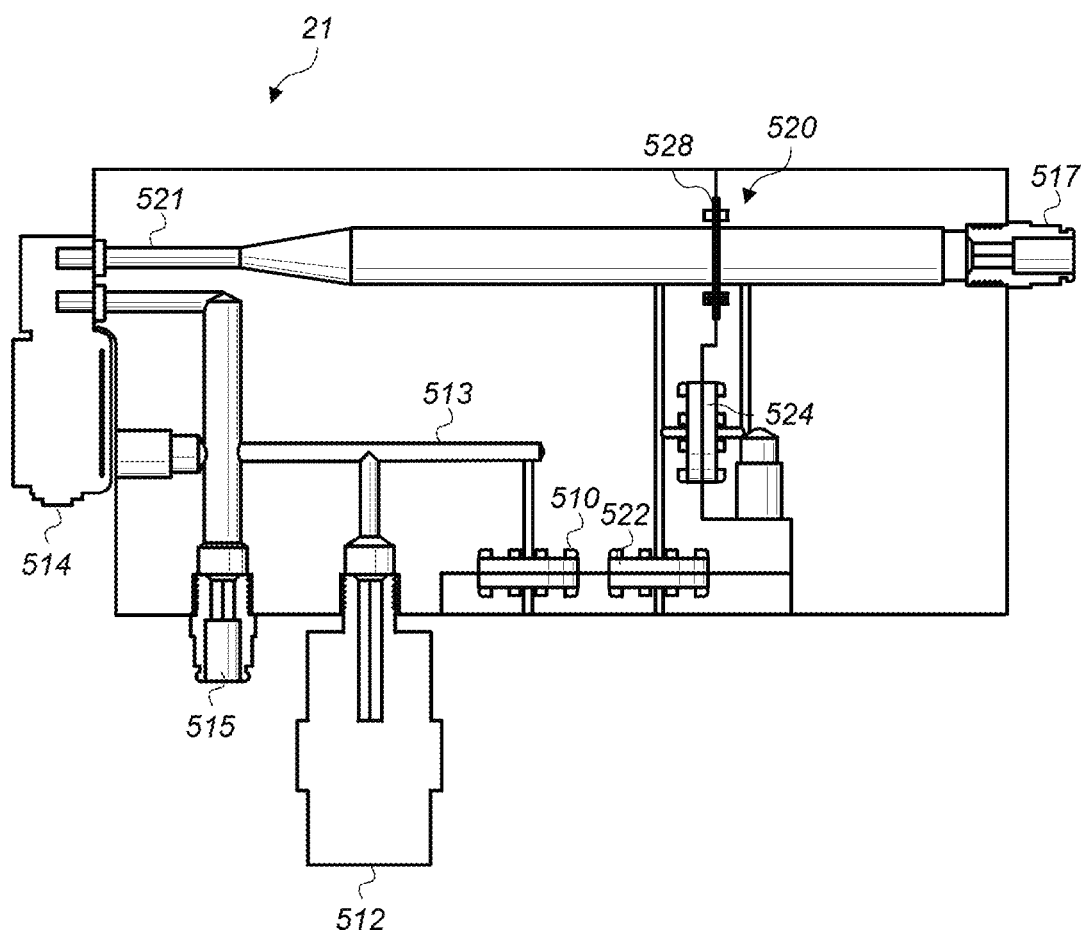
FIG. 9 depicts a cross sectional view of ventilation control system.

FIG. 9 depicts a cross sectional view of ventilation control system 21. Following the gas flow path, gas enters the ventilation control system via gas inlet 515. Initially the system is in a parked or non-active state and proportional valve 514 is closed. This allows the conduits 513 to become filled with gas and pressurized. When the pressure in the conduits reaches a predetermined value (e.g., 50 psi) the controller activates the system, opening proportion valve 514. Pressure gauge 510 measure the pressure in conduits 513 which represents the feed gas pressure for the ventilator system.

Once activated, proportional valve release air/oxygen into conduit 512 which conveys the gas to the pressure differential system 520. As discussed above, pressure differential system includes a first (high pressure side) pressure sensor 522 and a second (mask side) pressure sensor 524 and a flow rate sensor 528. After passing through pressure differential system 520, the air/oxygen passes out of the ventilation control system via outlet port 517.

Figure 10:
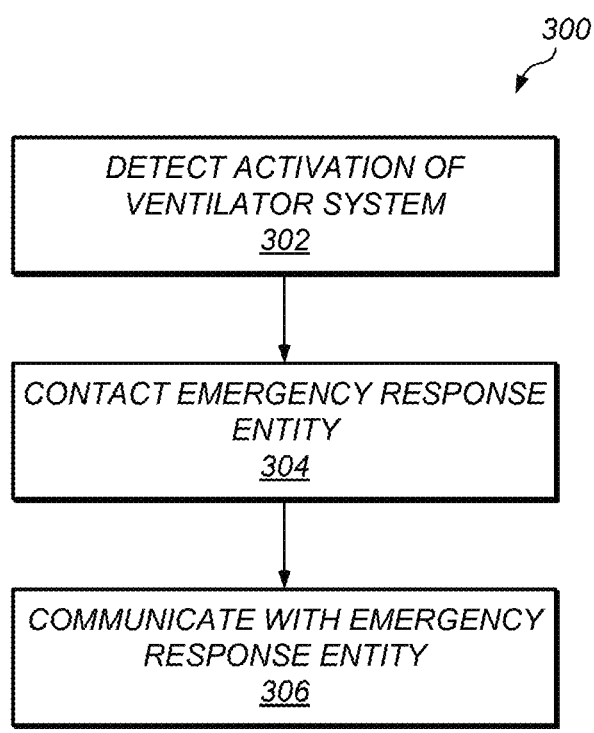
FIG. 10 is a flow chart illustrating a method of operating the ventilator system in one embodiment.

FIG. 10 is a flow chart illustrating a method of operating the ventilator system in one embodiment (see method 300). At 302, activation of a ventilator system is detected (e.g., ventilator system 10 described above relative to FIGS. 6A-6E). At 304, the system contacts an emergency response entity. At 306, a communication is made with the emergency response entity. In certain embodiments, the communication with emergency response entity is carried out over a communication network connecting a ventilator system (e.g., ventilator system 10.)

Systems and Methods for Performing CPR with Measures to Control Timing and Transitions Between Artificial Respirations and Chest Compressions In some embodiments, a ventilator system provides signals to a person performing compressions, manual control of an artificial respiration sequence, or both, to minimize non compression, non-respiration time during CPR. Various embodiments may enable rescuers to do compressions up to the point the positive pressure respiratory phase begins. In some embodiments, the compressor (that is, the rescue person performing the compressions) has flexibility in the number of compressions performed. For example, in one embodiment, the number of compressions may be adjusted between 25 and 30. In some embodiments, the ventilator includes a manual trigger that allows the rescuer to manually activate the breath delivery at a time that reduces or minimizes non-compression, non-respiratory time.

1. Signaling a Person Performing Compressions During CPR

In some embodiments, a ventilator system provides signals to a compressor for when it is acceptable to perform compressions. The signal may be, for example, a light, sound, or symbol that tells the rescuer when to do compressions, and/or when not to do compressions. A notification not to compress would start at some point immediately prior to the initiation of the of the positive pressure phase of the respiratory cycle. At that time, in response to the signal, the compressor would then stop performing compressions. This notification would continue until the end of the positive pressure phase of the cycle. The notification to start compressing would then become active. The signals can be used to minimize the time when compressions and respirations are not being performed. Without this technology, there can be up to a five second delay in initiating compressions after the breath is given.

In some embodiments, a ventilator system provides signals to notify rescue personnel when to perform compressions in relation to the respiratory cycle. Examples of signals include, in various embodiments, an audible signal, a visual-light on/off, different colored lights for compressions and respirations, or a symbol that changes to show compression or respiration. In some embodiments, the signals include audible instructions. For example, the signaling device may generate a "Start Compressions Now" instruction when the system has determined compressions should start, a "Stop Compressions Now" instruction when the system has determined that compressions stop, and so on. In some embodiments, a system gives a signal to not perform compressions. For example, a system may give a signal to not perform compressions during a period when inspiration will be occurring.

In some embodiments, a signaling mechanism provides instructions on how many compressions to perform, or duration of compressions, based on information about respirations being performed by a ventilator.

In certain embodiments, a rescuer may be presented with a graphical display that provides queues and instructions relating to timing of compressions. For example, a time graph may show a rescuer a moving line representing the current time sweeping across a graph, converging on a fixed line on the graph that indicates when the next set of compressions should begin. The graphical display may also include a display of measured information about operation of the ventilator, for example, from pressure sensors in the ventilator.

In some embodiments, the signaling device is built into a ventilator. In some embodiments, the signaling device is in a device that connects with, but is separate from, the ventilator. In one embodiment, the signaling device is a stand-alone device.

Figure 11:
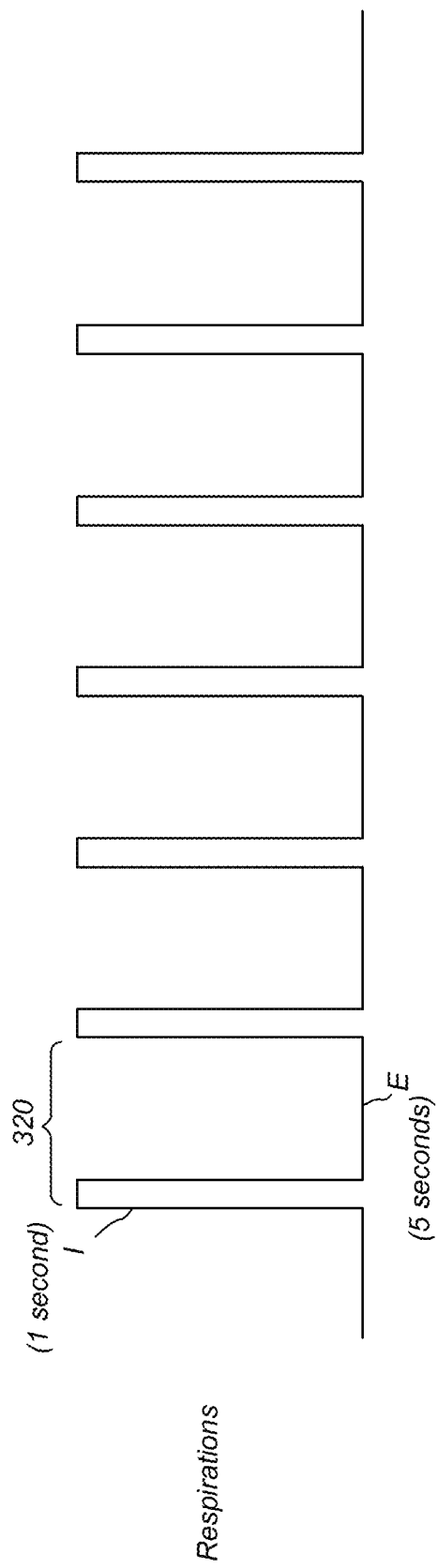
FIG. 11 illustrates artificial respiration by a ventilator in some embodiments.

FIG. 11 illustrates artificial respiration by a ventilator in some embodiments. In FIG. 11, each artificial respiration cycle 320 includes inspiratory phase I and expiratory phase expiratory phase E. The ventilator continuously repeats the artificial respirations until the ventilator is shut off by rescue personnel. In the inspiratory phase, the ventilator produces positive pressure to supply oxygen to the person's lungs. In the expiratory phase, the ventilator produces no or low pressure. In this example, each inspiratory phase is about 1 second in duration and each expiratory phase is about 5 seconds in duration in accordance with the protocols of artificial respirations as established by the American Heart Association.

Figure 12:
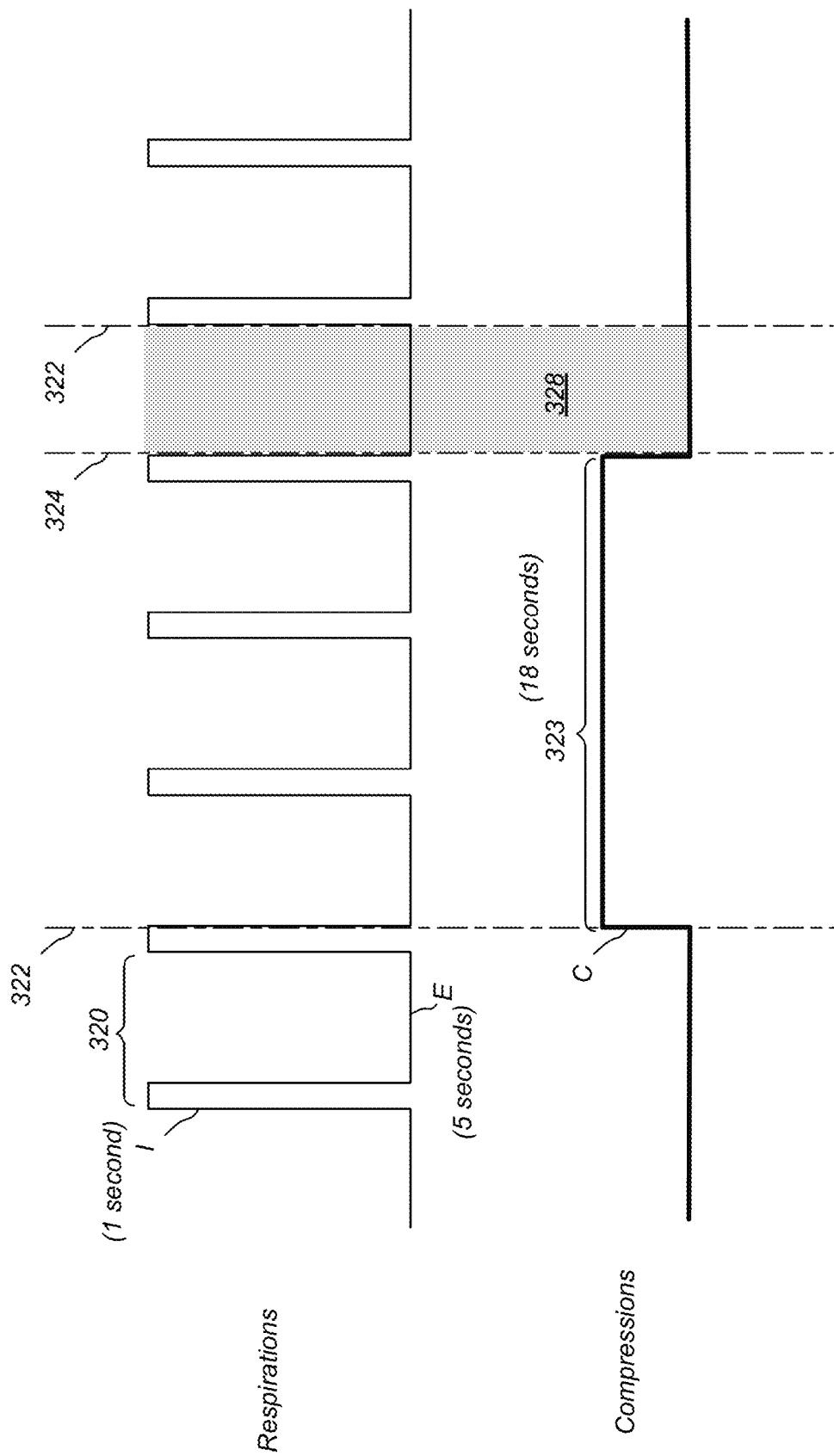
FIG. 12 illustrates one compression pattern for a ventilator using the artificial respiration cycle.

FIG. 12 illustrates one compression pattern for a ventilator using the artificial respiration cycle shown in FIG. 12 and one standard protocol for timing of compressions. At point 322, according to the protocol for this example, at the end of the second inspiratory phase, the compressor performs 30 compressions C at a rate of 100 compressions per minute, as per American Heart Association protocols. At this rate, the total duration C of compressions is about 18 seconds. Using this protocol, the compressor thus finishes the prescribed number of compressions at time 324, about 5 seconds before the next inspiratory phase by the ventilator will start at 326. Interval 328 is therefore a non-breathing, non-compression interval.

Figure 13:
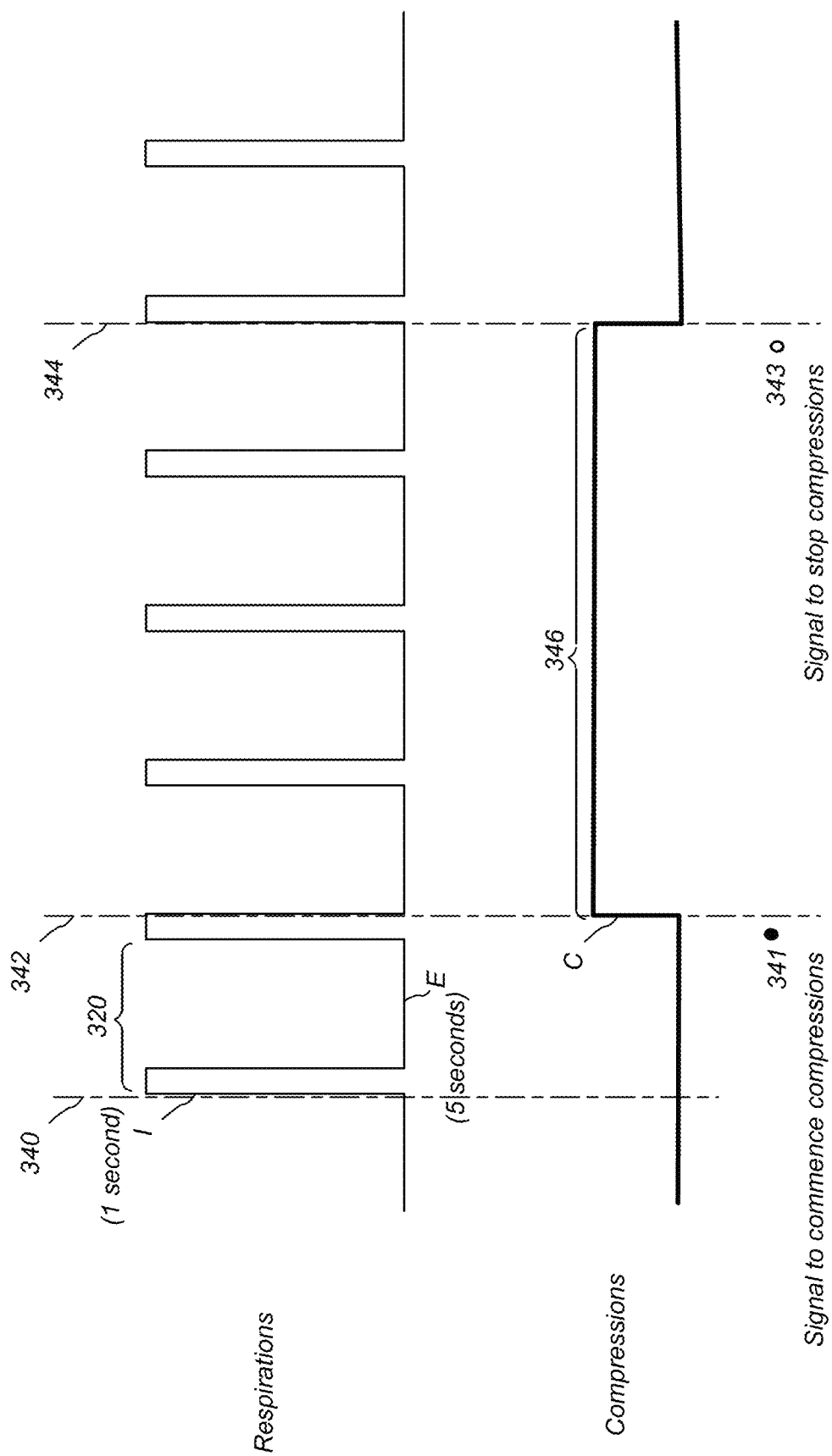
FIG. 13 illustrates a signal used to signal compressions according to one embodiment.

Fixed Artificial Respiration Interval and Fixed Interval Between Artificial Respirations—the Rescuer Follows Signals to Keep Compressing During the Whole Interval FIG. 13 illustrates a signal used to signal compressions according to one embodiment. Initially, one or two inspiratory phases are given 340. At or in advance of time 342, the compressor is given a signal 341 (for example, an audible queue) instructing the compressor to commence compressions at time 342. The compressor performs compressions at the prescribed rate until a second signal 343 is given at or in advance of time 344, to stop chest compressions at time 344. At time 344, the compressor suspends chest compressions. Also, at time 344, another artificial respiration sequence begins. The signaling pattern is repeated in synchronization with the ventilator respiration cycles. In some embodiments, signals 341 and 343 are chosen to minimize the amount of non-compression, non-breathing time during the CPR procedure. The pause of 4 seconds at 346 should is only meant for explanation purposes. This cycle could be more or less and may correspond to prevailing standards of CPR.

The content of the signals 341 and 343 may guide the compressor in starting and stopping the compressions at the right time. In one embodiment, for example, signals 341 and 343 include a countdown (for example, signal 341 may be "3 . . . 2 . . . 1 . . . compress") or one or more beeps or tones a prescribed interval in front of the time at which the compressor is to act. In other embodiments, the compressor may be given an audible word command to "Stop compressions" just as the first inspiratory phase commences and an audible word command to "Start compressions" just after the last inspiratory phase ends. Another embodiment might use mechanical signals, rotating symbols, pictures or graphic displays that show color or pictures which indicate when to compress and when to ventilate or hold compressions.

The following is another example of a procedure using signaling according to one embodiment:

With Continuous Breath Delivery without Pauses for Compressions:

Compress for 25 compressions, at the count of 25 compressions continue until the person performing artificial respirations identifies the signal from the device that the next positive pressure phase is about to begin. (This will give between 25-30 compressions). Immediately prior to the positive pressure phase of the breath, the device will give the signal to stop compressions. When the person operating the device sees the signal to stop compressions, the person notifies the compressor to hold compressions. The positive pressure phase will cycle and the breath will be given. At the end of the positive pressure phase, the notification to perform compressions will begin, but because two breaths need to be given, this first notification is ignored. At the initiation of the next breath, the hold compressions notification will be given. At the completion of this second positive pressure phase, the notification to begin compressions will be given. The person using the device will then give the command to continue compressions.

2. Artificial Respiration with Intermittent Breath Delivery

In some embodiments, a ventilator system has a manual trigger that activates a sequence of two or more breaths. For example, in one embodiment, a system includes a button that an operator can push that generates a set number of breaths. In one embodiment, the system produces two breaths with each activation. In another embodiment, the system generates a preset number of breaths followed by a preset pause during which time compressions are given. This preset pause is, in one embodiment, built into the default setting. As used herein, "intermittent" may, in various embodiments, include a regular or irregular interruption.

In some embodiments, a ventilator continuously cycles until the supply of oxygen is switched off or deactivated. In one embodiment, oxygen flow is turned on and the mask is attached. The ventilator continuously delivers breaths until the mask is removed or oxygen is turned off. When chest compressions are being performed the seal of the mask is released so that breath is vented to the environment.

Each Manual Trigger Produces One Sequence of Artificial Respiration with a Pre-Determined Number of Inspiration Phases; Manually Re-Trigger Respiration when Compressor Finishes.

Figure 14:
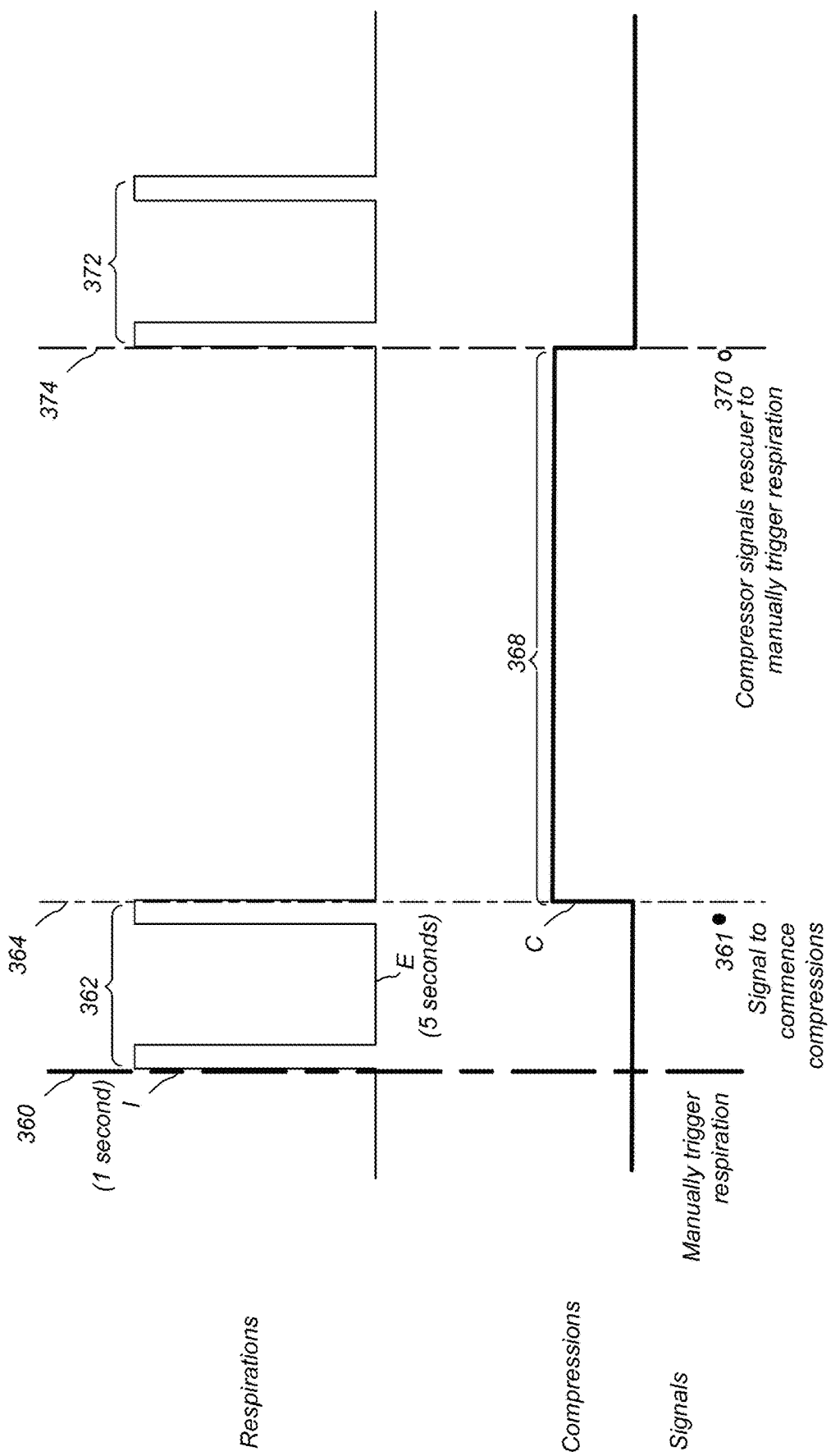
FIG. 14 there are two inspirations per respiration sequence, a system may in some embodiments include any number inspiration phases.

In some embodiments, each manual trigger of a ventilator generates a single respiration sequence having a pre-determined number of inspiratory phases. For example, the manual trigger may activate an inspiratory phase 1-expiratory phase-inspiratory phase 2, then suspend until such time the ventilator is manually retriggered. With this system, the compressor may perform a predetermined number or duration of compressions, then immediately signal that the ventilator be re-triggered to generate another inspiratory-expiratory-inspiratory sequence. FIG. 14 illustrates a series in which each manual trigger activates one respiration sequence having two inspiration phases. At time 360, a manual trigger is pressed. In response to the manual trigger, the ventilator performs sequence 362, which includes two inspiratory phases with an intervening expiratory phase. At the end of the second inspiratory phase of sequence 362, start compression signal 361 is given to the compressor to perform a specified number or duration of compressions, which continue for interval 368. Once the prescribed number or duration of compressions has been accomplished during interval 368, the compressor may signal to the rescuer handling the ventilator to perform a manual retrigger at 370. Upon retriggering at 370, a new sequence 372 of artificial respiration is commenced at time 374. The sequence triggered at 372 may have the same cycle as the sequence triggered at 362.

Although in FIG. 14 there are two inspirations per respiration sequence, a system may in some embodiments include any number inspiration phases. In one embodiment, each manual trigger produces a sequence having three inspiratory phases with two intervening expiratory phases.

Figure 15:
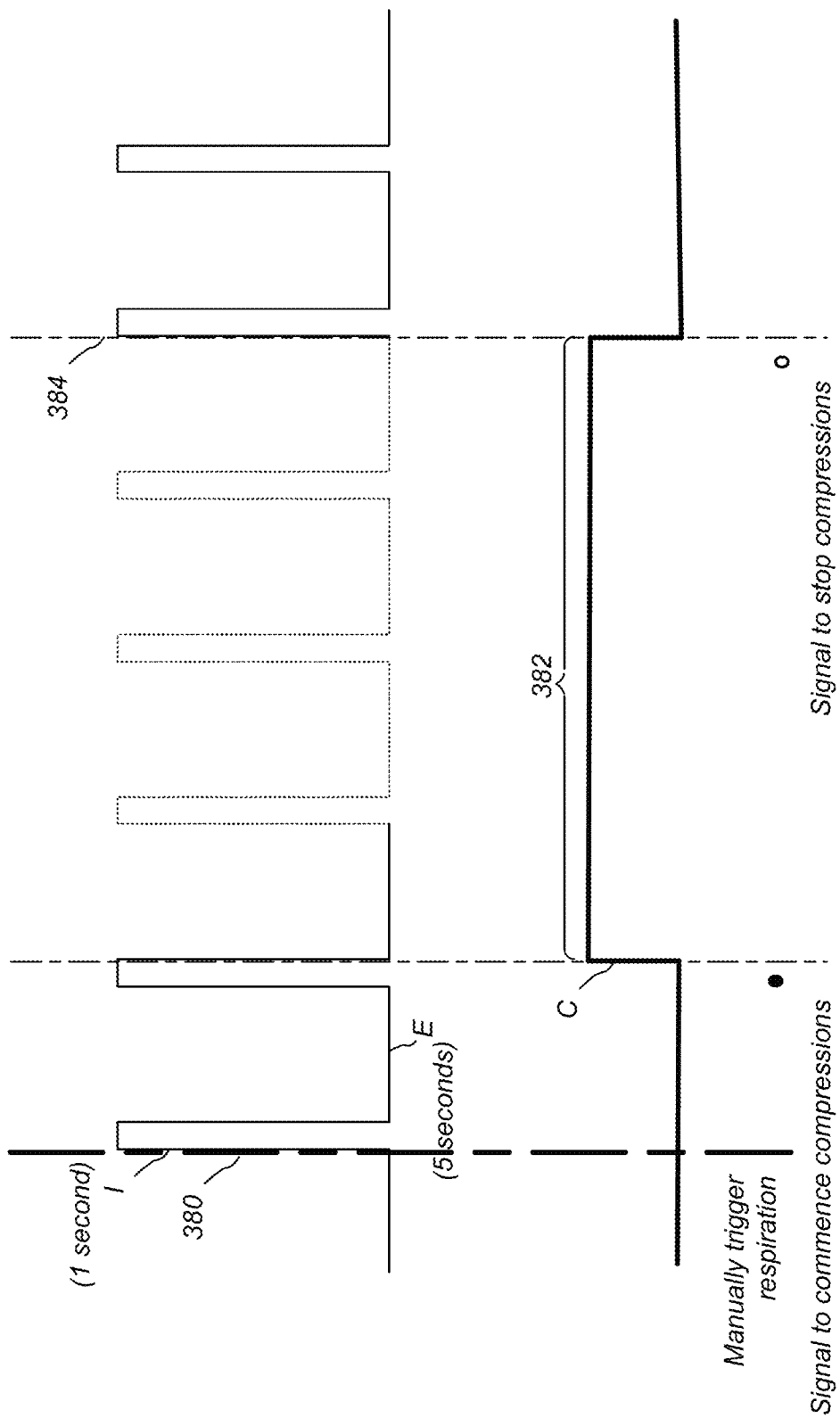
FIG. 15 illustrates one embodiment of a CPR process with continuous alternating respiration/compression cycles from an initial initiation of function of ventilation control system.

One Manual Trigger Generates Continuous Alternating Respiration Sequences/Compression Periods In some embodiments, the ventilation control system delivers continuous alternating respiration/compression cycles with a pre-determined number of inspiratory phases in the respiration phase, and a pre-determined period when inspirations are suspended to allow compressions. Initiation of function of the ventilation control system may be manually triggered, or may result from the initiation of air/oxygen flow and coupling of the mask to the ventilation control system. FIG. 15 illustrates one embodiment of a CPR process with continuous alternating respiration/compression cycles from an initial initiation of function of ventilation control system. At 380, respiration is manually triggered and the first inspiratory cycle commences. While compressions are being performed in interval 382, the mask may separate from the person receiving compressions until the next respiration at 384. Compression guidance signals may be given at end of the last inspiratory phase of a cycle and at the prior to the beginning of next respiration sequence.

In some embodiments, a system includes an adjustment mechanism that allows the user to set the duration for compression between inspiratory phases. For example, a user may be able to adjust the time between the last inspiration of one respiration sequence and the first inspiration of the next sequence. The user, or someone trained to adjust the device, may also be able to set the number of inspiratory phases-in a sequence and/or the interval between inspiratory phases, the pressure level of each inspiratory phase, or other parameters. Ability to change settings is not required to utilize ventilation control system, but would allow for changes to settings to coincide with changes in accepted CPR parameters.

The following are examples of procedures using intermittent breath delivery according to some embodiments:

With Intermittent Breath Delivery where One Activation Yields One Respiratory Cycle:

Compress for 30 (or however many is protocol) compressions, after which the command will be given to the person using the device will activate the device. The device will be activated and give a set number of breaths. At the end of the positive pressure phase of the last breath, the device will give the signal to give compressions. After the last compression the command will be given to activate the device to start the next cycle.

With Intermittent Breath Delivery where Activation Yields Continuous Intermittent Cycling.

Compress until the device gives the signal that the next breath cycle is about to start. The person using the device gives the command to stop compressions. The device delivers the appropriate number of breaths. At the end of the positive pressure phase of the last breath the device gives the signal to continue compressions. The person using the device tells the person doing compressions to continue compressions. Compressions are performed until the device gives the signal to hold compressions.

Figure 16:
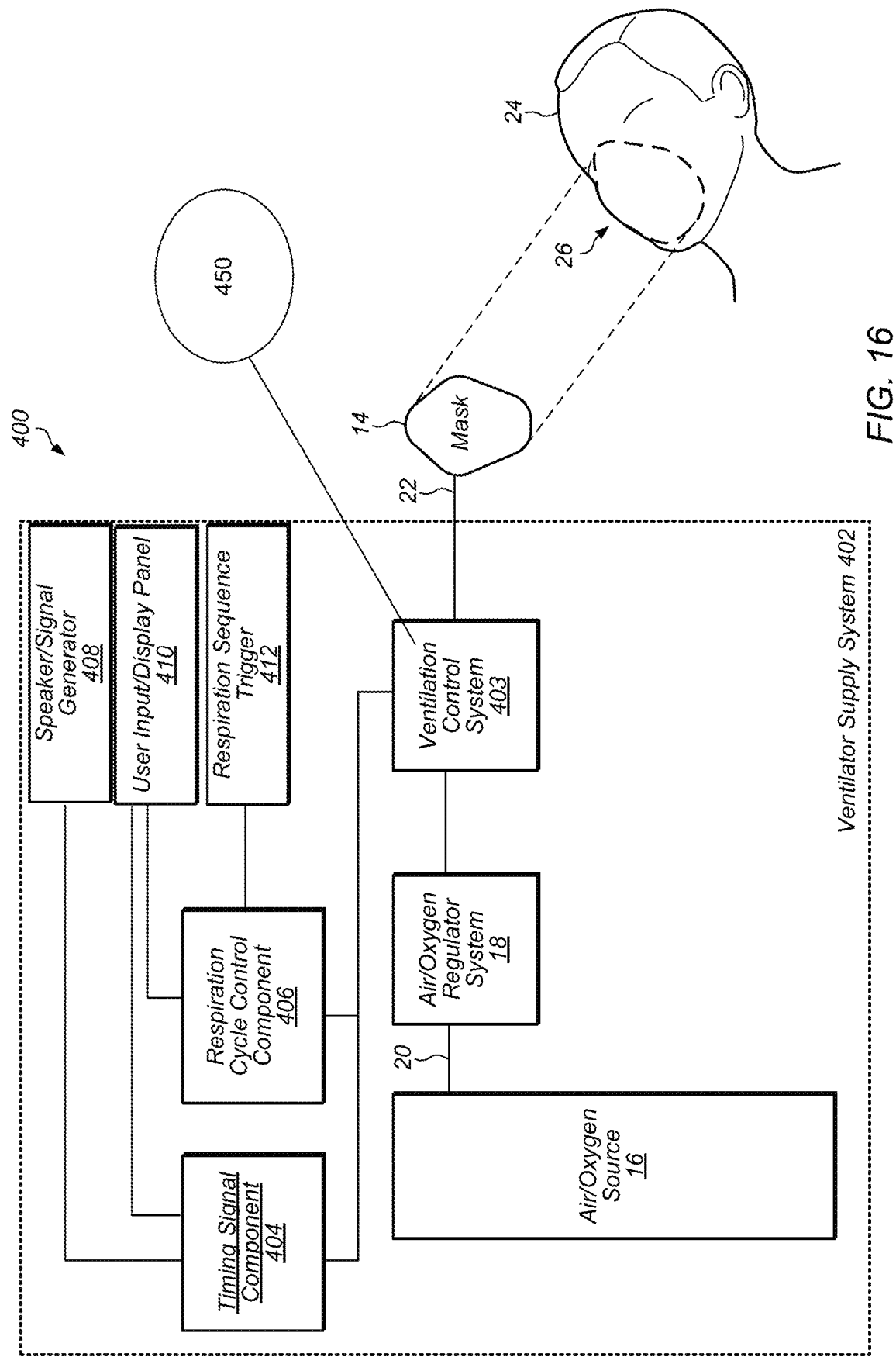
FIG. 16 illustrates one embodiment of a ventilator system that can be used in CPR with elements to control timing and transitions between respirations and chest compressions.

FIG. 16 illustrates one embodiment of a ventilator system that can be used in CPR with elements to control timing and transitions between respirations and chest compressions. The ventilator system 400 includes a ventilator supply system 402 and a ventilator mask 14. Source and regulation elements may be as described above relative to FIG. 1. Ventilator mask 14 may be similar to that described above relative to FIG. 1. Ventilator supply system 402 includes air/oxygen source 16, air/oxygen regulator system 18, ventilation control system 403, timing signal component 404, respiration cycle control component 406, speaker/signal generator 408, user input/display panel 410, and respiration sequence trigger 412.

Timing signal component 404 may compute and determine one or more signals to be given to a compressor relating to the timing of chest compressions. The signals may be displayed on user input/display panel 410, delivered to a rescuer by way of speaker/signal generator 408, or combinations thereof. In one embodiment, signals are visible-only (non-audible signal).

Respiration cycle control component 406 may control activation of respiration sequences by the ventilator. Respiration cycle control component 406 may provide signals to the ventilation control system 403 to start and stop each sequence of respirations. In some embodiments, respiration cycle control component 406 controls the number, duration, timing, and/or pressure levels of inspiratory phases and expiratory phases. Respiration cycle control component 406 may receive activation signals from respiration sequence trigger 412. Respiration sequence trigger 412 may be, in one embodiment, a push button.

In FIG. 16, components relating to timing of the compressions and synchronization between respirations and chest compressions are included in the ventilator supply system 402. In certain embodiments, the timing signal component, respiration cycle control component, triggers, and/or user interface elements may be in a device or system that is separate from the basic ventilator components, such as air/oxygen source 16, air/oxygen regulator system 18. In certain embodiments, a separate timing respiration or compression timing device receives data or signals from a separate ventilator. In certain embodiments, timing components of a system receive sensor data from the ventilator, for example, pressure sensors. The sensor data may be used to determine timing of compression signals, respirations, or both. For example, for a ventilator that is set up to provide a continuous cycle of alternating inspirations/exhalations, the timing component may use sensor data to establish timing of the respiration cycle.

In some embodiments, a compression sensor 450 is coupled to the ventilation control system. Compression sensor 450, during use, is placed on the subject's chest in the location that the compressions are being administered to the subject. Compression sensor 450 includes one or more sensors that detect the application and release of pressure applied to the compression sensor. As previously discussed, it can be important that the induced respirations are discontinued when compressions are being applied. To reduce the chance of undesirable respiration during compressions, compression sensor is coupled to ventilation control system 403. When compressions sensor 450 detects a compression, ventilation control system 403 stops the respirations until the compression sensor indicates that no more compressions are being applied. For example, if no compressions are detected after a period of 1-2 seconds, then the respiration cycle is continued. This allows the caregiver to focus on the proper resuscitation sequence without having to worry about making adjustments to the device.

In some embodiments, a ventilator system includes a mechanism for adjusting parameters. For example, a ventilator system may allow for adjustment by a technician to change the volume per breath, number of breaths per minute, or other parameter. In some embodiments, a parameter is changed based on standards set by a medical organization, such as the American Heart Association ("AHA"). For example, if the AHA were to decide to change the parameters for adult rescue breathing from a breath of 600 cc for adults to 500 cc, a technician would use the adjustment mechanism on the device to change the volume per breath.

In some embodiments, a ventilator system allows for multiple settings for one or more parameters. The system may include default settings for each parameter that can be changed. In some embodiments, the default setting is set by a technician or by the user. In certain embodiments, the default setting is selected by the selection or attachment of a particular mask (e.g., child mask or an adult mask).

Adjustments may be made mechanically, electrically, or by another manner, or by a combination thereof. In certain embodiments, adjustments are made by a separate device that is electronically connected to a ventilator system (for example, a personal computer connected by way of a cable or over a computer network.)

In some embodiments, the settings can be adjusted internally by a technician, but not by a user. A technician may, for example, pop the device open and adjust the settings, but the settings may still be preset for the user. In some cases, all field units can be adjusted without having to replace the units in their entirety. In other embodiments, default settings can be adjusted by the user to comply with changes to accepted standards of artificial respirations.

In some embodiments, a system provides oxygen to someone who needs supplemental oxygen, but does not need CPR. As an example, the system may be used to perform CPR on a drowning victim, and, after some medical attention has been given, the victim begins to breathe on their own. In this case, a system may be used to provide supplemental continuous high-flow oxygen via face mask, even after the victim no longer needs positive pressure breaths via artificial respiration. A supplemental oxygen mask may be or include, in various embodiments, a non re-breather mask, respiratory care mask, or nasal cannula. In some embodiments, a device is keyed to provide continuous high flow oxygen via the supplemental oxygen mask. In some embodiments, a non re-breather mask is used to provide supplemental oxygen to a spontaneously breathing person.

In some embodiments, a system for providing medical assistance operates in two or more modes including a ventilation mode (e.g., artificial respiration) or a supplemental oxygen mode. In one embodiment of using a dual-mode system, a person may first administered air or oxygen in a ventilation mode, with artificial respiration provided using the system. For a person that needs supplemental oxygen but does not need CPR, or for the person which no longer needs CPR (e.g., the person is breathing on their own), a supplemental oxygen mode is activated to provide continuous oxygen to the person. In some embodiments, the supplemental oxygen mode is activated automatically when the system keying mechanism detects that the supplemental oxygen mask has been coupled to the system.

Figure 17:
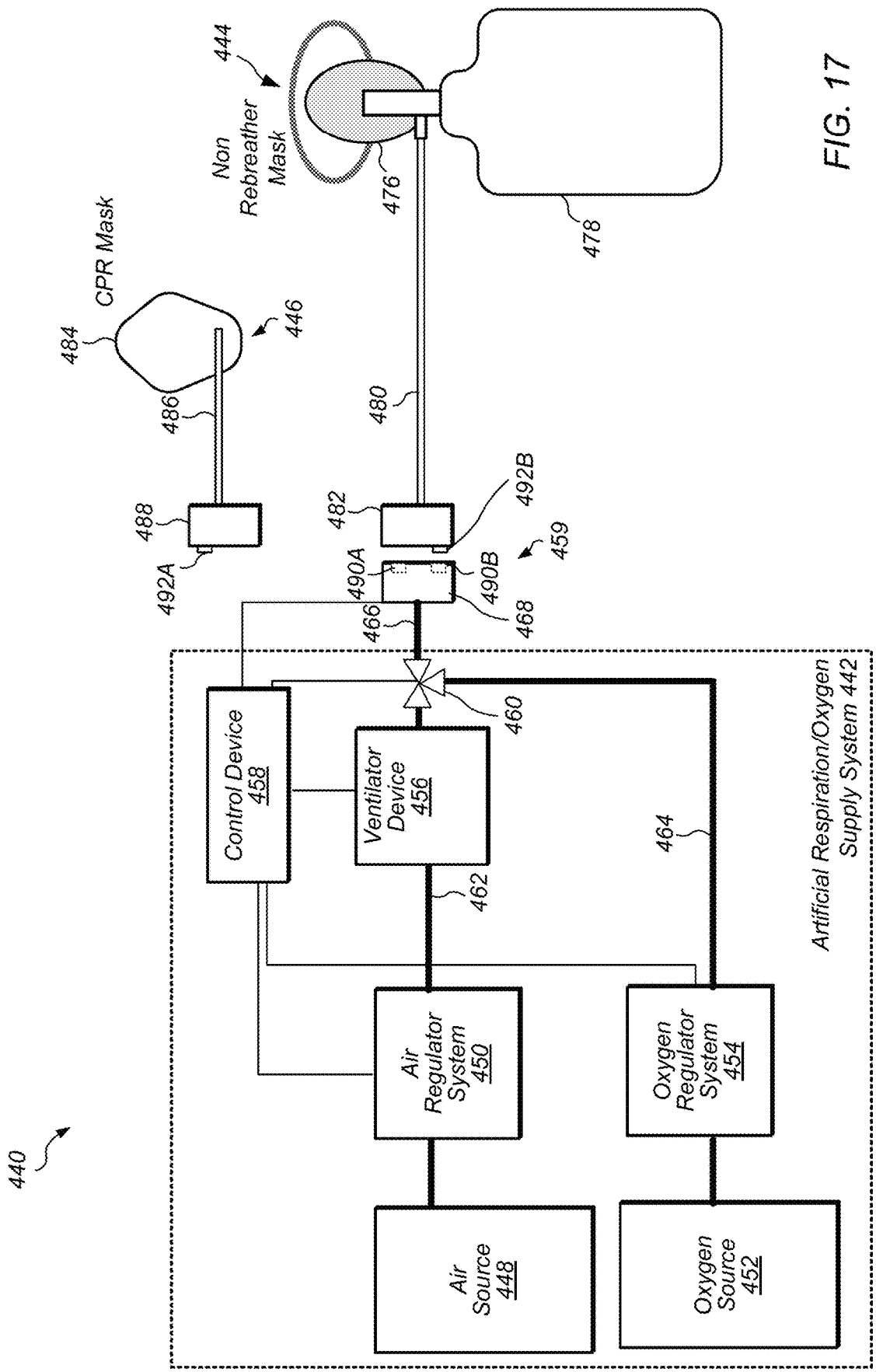
FIG. 17 illustrates one embodiment of a system that can be used to provide artificial respiration or continuous oxygen in modes initiated by installing different masks.

FIG. 17 illustrates one embodiment of a system that can be used to provide artificial respiration or continuous oxygen in modes initiated by installing different masks. One or more of the masks may be a ventilator mask used during artificial respiration, and another mask may be supplemental oxygen mask for providing oxygen to a person who is breathing spontaneously.

System 440 includes artificial respiration/oxygen supply system 442, non rebreather mask assembly 444, and CPR mask assembly 446. Either non-rebreather mask assembly 444 or CPR mask assembly 446 may be coupled to artificial respiration/oxygen supply system 442 to receive air and/or oxygen supplied by artificial respiration/oxygen supply system 442. In various embodiments, the mask that is coupled may be chosen depending on the condition of the patient and/or size of the patient.

Artificial respiration/oxygen supply system 442 includes air source 448, air regulator system 450, and/or oxygen source 452, oxygen regulator system 454, ventilator device 456, and control device 458. Port 459 is provided for delivery of air and/or oxygen to a person wearing one of the masks of non-rebreather mask assembly 444 or CPR mask assembly 446.

Ventilator device 456 can be operated to provide air from air source 448 to masks by way of line 462, line 466, and port 459. In some embodiments, port 459 is a receptacle on the case of the ventilator system. A port may, however, include any opening used to supply air/oxygen to a mask assembly. In certain embodiments, port 459 is included in a fluid connector at the end of a hose. Artificial respiration/oxygen supply system 442 can be operated to provide oxygen from oxygen source 452 to a person wearing one of the masks by way of line 464, line 466, and port 459. Valve 460 may be operated to control flow from the sources.

Control device 458 may be used to control the output of artificial respiration/oxygen supply system 442. Control device 458 may be implemented in a combination of two or more control devices. Control device 458 may be one or more manual devices, electronic devices, pneumatic devices, and/or combinations thereof. In certain embodiments, control device 458 is entirely manual. For example, a control device may include one or more manually operated valves, clamps, squeeze bottles, etc. In other embodiments, a control device includes electrical components. For example, in some embodiments, the system includes a microprocessor that controls the output of the system, mode of operation, and/or signaling to rescue personnel based on a set of rules reflected in program instructions.

For illustrative purposes, artificial respiration/oxygen supply system 442 includes a ventilator that receives air from an air source, and a separate oxygen source that can supply oxygen for supplemental oxygen to a non rebreather mask. An artificial respiration/oxygen supply system may, however, in certain embodiments supply only oxygen during ventilation or supplemental oxygen mode. In some embodiments, the supply for both artificial respiration and supplemental oxygen are provided from the same source (e.g., the same oxygen tank is used for both supplemental oxygen and artificial respiration).

Non-rebreather mask assembly 444 includes non-rebreather mask 476, reservoir bag 478, hose 480, and non-rebreather connector 482. Non-rebreather mask assembly 444 may include one or more valves to allow unassisted breathing by the wearer. The valves may prevent inhalation of room air and/or re-inhalation.

In one embodiment, one end of the connector is tapered to fit into the opening at the end of the oxygen tubing. The larger end connects to the oxygen source. As discussed above, the identification of a mask is automatically performed by the ventilation system based on a change in pressure due to a gas flow restrictor placed in the gas flow path. In an embodiment, connector 482 of non-breather mask assembly 444 includes gas flow restrictor (not shown). During use, when mask 444 is coupled to conduit 525, the gas flow restrictor causes the pressure in the conduit, and thus on the mask side of the pressure differential system increase. The amount of the pressure increase is proportional to the gas flow restrictor that is coupled to the mask, and thus, as described earlier, can be used by the system controller to identify the mask being applied to the subject.

CPR mask assembly 446 includes CPR mask 484, hose 486, and CPR connector 488. CPR mask 484 may serve as a ventilator mask for artificial respiration of a person receiving CPR. The identification of CPR mask 484 is automatically performed by the ventilation system based on a change in pressure due to a gas flow restrictor placed in the gas flow path.

In one embodiment, when non-rebreather mask assembly 444 is coupled to artificial respiration/oxygen supply system 442, the system uses the change in pressure to detect which non-rebreather mask is connected. Based on this, the system may deliver supplemental oxygen to the person wearing non-rebreather mask 476. In a system having multiple non-rebreather masks of varying sizes, each size mask may have a different flow restrictor so that the change in pressure caused by each type of non-rebreather masks can be used to detect which size non-rebreather mask is connected. The oxygen flow characteristics may be set accordingly. For example, a greater the flow of oxygen may be supplied for a large mask than for a small mask.

In certain embodiments, an artificial respiration/oxygen supply system includes a keying mechanism. Keying mechanisms may be, for example, as described herein or in U.S. Pat. No. 8,707,954 or 8,844,521 to McCarthy, which are incorporated herein by reference. The keying mechanism may be used to control which the mode of operation a system is operating, characteristics of the flow from the system (for example, flow rate, pressure, percent oxygen, inspiration time, cycle time, etc.) In various embodiments, a CPR mask may or may not have a hose. The small end of a connector may be connected to the non-rebreather mask and the large end may be keyed to fit into the same opening as the CPR masks. When attached the keying feature may key to the delivery of continuous oxygen flow. Keying to size of different masks (for example, different sizes for adults, infants) may be included in various embodiments In the embodiment shown in FIG. 16, port connector 468 includes keying elements 490A and 490B. Keying element 490A on port connector 468 may match complementary keying element 492A on CPR mask assembly 446. Keying element 490B on port connector 468 may match complementary keying element 492B of non-rebreather mask connector 482. Keying elements 490A and 490B may be, in some embodiments, slots, grooves, or pockets, and keying elements 492A and 492B of non-rebreather mask assembly may be bumps, tabs, or ridges that are complementary in location, shape, and/or size to keying elements 490A and 490B, respectively. A keying mechanism may also include a sensor or other device that provides a signal to control device 458 when one of keying elements 490A is paired with a corresponding keying element on a mask assembly. The signal may be used to by the system for controlling output (for example, operating mode, oxygen or air characteristics, or both) of an air/oxygen supply system. In some embodiments, a system using electric, magnetic or RFID signals to sense which mask assembly is coupled to the system. In other embodiments, a keying mechanism uses a mechanical or fluid device to control the output.

In one embodiment, when non-rebreather mask assembly 444 is coupled to artificial respiration/oxygen supply system 442, keying element 490B on port connector 468 aligns or mates with complementary keying element 492B on non-rebreather mask connector 482 of non-rebreather mask assembly 444. Upon connection, the system uses the keying mechanism to detect that the non-rebreather mask is connected. Based on this, the system may deliver supplemental oxygen to the person wearing non-rebreather mask 476. In a system having multiple non-rebreather masks of varying sizes, each size mask may have a different key so that the keying mechanism can detect which size non-rebreather mask is connected. The oxygen flow characteristics may be set accordingly. For example, a greater the flow of oxygen may be supplied for a large mask than for a small mask.

In a similar manner to that described above with respect to the non-rebreather masks, when CPR mask assembly 446 is coupled to artificial respiration/oxygen supply system 442, keying element 490A on port connector 468 may align or mate with complementary keying element 492A on CPR mask connector 488 of CPR mask assembly 446. The system may detect that a ventilator mask is installed (and, in some cases) which CPR mask is installed, and set flow characteristics accordingly.

In a similar manner to that described above with respect to the non-rebreather masks, when CPR mask assembly 446 is coupled to artificial respiration/oxygen supply system 442, the system may detect that a ventilator mask is installed (and, in some cases) which CPR mask is installed, and set flow characteristics accordingly.

In some cases, the system provides signals to rescue personnel, including, for example, instructions for performing chest compressions and/or artificial respirations. In some embodiments. The system may also provide instructions to connect a supplemental oxygen mask, or information relating to the flow of such supplemental oxygen.

In certain embodiments, an air/oxygen supply system includes multiple receptacles to allow both a non-rebreather mask and a CPR mask to be coupled to the system at the same time. The system may include a control that allows a user to switch on or off the supply to either of the masks, or to select which mask is to receive an air/oxygen supply at a given time.

In some embodiments, components of system described herein (for example, ventilator supply system 402) may be implemented in one or more computing devices. Computing devices may, in various embodiments, include components such as a CPU with an associated memory medium such as Compact Disc Read-Only Memory (CD-ROM). The memory medium may store program instructions for computer programs. The program instructions may be executable by the CPU. Computer systems may further include a display device such as monitor, an alphanumeric input device such as keyboard, and a directional input device such as mouse. Computer systems may be operable to execute the computer programs to implement computer-implemented systems and methods. A computer system may allow access to users by way of any browser or operating system.

Computer systems may include a memory medium on which computer programs according to various embodiments may be stored. The term "memory medium" is intended to include an installation medium, e.g., Compact Disc Read Only Memories (CD-ROMs), a computer system memory such as Dynamic Random Access Memory (DRAM), Static Random Access Memory (SRAM), Extended Data Out Random Access Memory (EDO RAM), Double Data Rate Random Access Memory (DDR RAM), Rambus Random Access Memory (RAM), etc., or a non-volatile memory such as a magnetic media, e.g., a hard drive or optical storage. The memory medium may also include other types of memory or combinations thereof. In addition, the memory medium may be located in a first computer, which executes the programs or may be located in a second different computer, which connects to the first computer over a network. In the latter instance, the second computer may provide the program instructions to the first computer for execution. A computer system may take various forms such as a personal computer system, mainframe computer system, workstation, network appliance, Internet appliance, personal digital assistant ("PDA"), television system or other device. In general, the term "computer system" may refer to any device having a processor that executes instructions from a memory medium.

The memory medium may store a software program or programs operable to implement embodiments as described herein. The software program(s) may be implemented in various ways, including, but not limited to, procedure-based techniques, component-based techniques, and/or object-oriented techniques, among others. For example, the software programs may be implemented using ActiveX controls, C++ objects, JavaBeans, Microsoft Foundation Classes (MFC), browser-based applications (e.g., Java applets), traditional programs, or other technologies or methodologies, as desired. A CPU executing code and data from the memory medium may include a means for creating and executing the software program or programs according to the embodiments described herein.

In some embodiments, systems and functions as described above are implemented without any electronic components.

In certain embodiments, for example, a system implements control of air/oxygen (e.g., inspiration volume, cycle time, etc.), signaling, keying and/or mode of operation by way of non-electronic mechanisms and methods. For example, in one embodiment, the system activates a supplemental oxygen mode by a pneumatic mechanism.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. The words "include", "including", and "includes" mean including, but not limited to. As used throughout this application, the singular forms "a", "an" and "the" include plural referents unless the content clearly indicates otherwise. Thus, for example, reference to "a mask" includes a combination of two or more masks. The term "coupled" means directly or indirectly connected.

What is claimed is:

1. A ventilator system, comprising:
   a set of two or more ventilator masks, wherein each of at least two of the ventilator masks is configured in a size that will fit upon a different range of sizes of human faces than at least one other ventilator mask in the set of two or more ventilator masks, wherein each of the at least two ventilator masks comprises a gas flow restrictor that is different from a gas flow restrictor of the other ventilator masks of the at least two ventilator masks; and
   a ventilator supply system, comprising:
      an air/oxygen source;
      a connector configured to couple with each of the at least two ventilator masks;
      an air/oxygen supply system comprising a detection system capable of determining a pressure differential created by the application of air/oxygen to a mask coupled to the ventilator supply system, wherein the detection system comprises:
         a flow meter which determines the rate of air/oxygen flowing through the detection system;
         a first pressure sensor, downstream from the flow meter; and
         a second pressure sensor, upstream from the flow meter;
         wherein the pressure differential is determined by measuring the difference between the pressure detected by the second pressure sensor and the pressure detected by the first pressure sensor, and
      a controller coupled to the detection system, wherein the controller determines, during use, which mask, among the two or more ventilator masks, is coupled to the air/oxygen supply system based on the pressure differential detected by the detection system.

2. The ventilator system of claim 1, wherein the gas flow restrictor comprises a variation in an internal diameter of the flow restrictor, from one ventilator mask to another, such that the back pressure caused by the air/oxygen flow to each of the ventilator masks is different.

3. The ventilator system of claim 1, wherein the controller is further configured to set, based on the size of the ventilator mask determined to be coupled to the air/oxygen supply system, a pre-selected maximum pressure limit, a pre-selected breath volume, or a pre-selected respiratory-rate to provide air/oxygen to the ventilator mask as a function of the size of the ventilator mask coupled to the air/oxygen supply system.

4. The ventilator system of claim 1, wherein the controller is further configured to provide air/oxygen to the ventilator mask at the pre-selected maximum pressure limit, the pre-selected breath volume, or the pre-selected respiratory-rate.

5. The ventilator system of claim 1, further comprising a mask conduit configured to couple the ventilator supply to the ventilator mask.

6. The ventilator system of claim 1, wherein the selected range of sizes comprises one of an infant-size range, a child-size range, and an adult-size range.

7. The ventilator system of claim 1, further comprising a signaling device, coupled to the controller, configured to transmit a signal indicating that the air/oxygen supply system is in need of service.

8. The ventilator system of claim 1, further comprising a signaling device, coupled to the controller, configured to transmit a signal corresponding to a measure of one or more observed air/oxygen flow parameters.

9. The ventilator system of claim 1, further comprising a signaling device, coupled to the controller, configured to transmit a signal indicating a condition of at least one of: blockage, proper flow, and/or leakage of air/oxygen.

10. The ventilator system of claim 1, further comprising a communication device configured to enable communication with one or more emergency response personnel.

11. The ventilator system of claim 1, further comprising a signaling mechanism configured to deliver one or more signals to a rescuer relating to timing of chest compressions of the person, wherein the timing of the chest compressions for at least one of the signals is based at least in part on a time of delivery of at least one of the artificial respirations.

12. The ventilator system of claim 1, wherein the signaling mechanism is further configured to deliver a signal to the controller, when chest compressions are detected, wherein, when chest compressions are detected the delivery of air/oxygen to the mask is discontinued.

13. A method, comprising:
   selecting a mask from a set of two or more ventilator masks, wherein each of at least two of the ventilator masks is configured in a size that will fit upon a different range of sizes of human faces than at least one other ventilator mask in the set of two or more ventilator masks, wherein each of the at least two ventilator masks comprises a gas flow restrictor that is different from a gas flow restrictor of the other ventilator masks of the at least two ventilator masks;
   coupling the selected ventilator mask to an air/oxygen supply system, wherein the air/oxygen supply system comprises a detection system capable of determining a pressure differential created by the application of air/oxygen to the mask, wherein the detection system comprises:
      a flow meter which determines the rate of air/oxygen flowing through the detection system;

a first pressure sensor, downstream from the flow meter; and a second pressure sensor, upstream from the flow meter;

wherein the pressure differential is determined by measuring the difference between the pressure detected by the second pressure sensor and the pressure detected by the first pressure sensor;

automatically determining which, among the two or more ventilator masks, is coupled to the air/oxygen supply system based on the pressure differential detected by the detection system;

automatically setting, based on the size of the ventilator mask determined to be coupled to the air/oxygen supply system, a pre-selected maximum pressure limit, a pre-selected breath volume, or a pre-selected respiratory-rate to provide air/oxygen to the ventilator mask as a function of the size of the ventilator mask coupled to the air/oxygen supply system; and automatically providing air/oxygen to the ventilator mask at the pre-selected maximum pressure limit, the pre-selected breath volume, or the pre-selected respiratory-rate.

14. The method of claim 13, wherein coupling the ventilator mask to the air/oxygen supply system comprises selecting mask having a size based on a fit of the mask to a face of a human subject, and coupling the selected mask to the air/oxygen supply system.

15. The method of claim 14, wherein the selected mask, when coupled to the air/oxygen supply system, interacts with the air/oxygen supply system to thereby initiate the pre-selected maximum pressure limit, breath volume, and respiratory-rate from the air/oxygen supply system.

16. The method of claim 13, wherein the mask size comprises one of a plurality of mask sizes.

17. The method of claim 16, wherein the plurality of mask sizes comprise one or more infant-size masks, one or more child-size masks, and one or more adult-size masks.

* * * * *